US012350300B2

(12) United States Patent
Lyte

(10) Patent No.: US 12,350,300 B2
(45) Date of Patent: *Jul. 8, 2025

(54) USE OF DOPAMINE PRODUCING PRODUCTS TO INCREASE VACCINE EFFICACY

(71) Applicant: Iowa State University Research Foundation, Inc., Ames, IA (US)

(72) Inventor: Mark Lyte, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/045,264

(22) Filed: Oct. 10, 2022

(65) Prior Publication Data

US 2023/0111960 A1      Apr. 13, 2023

Related U.S. Application Data

(60) Provisional application No. 63/262,301, filed on Oct. 8, 2021.

(51) Int. Cl.
*A61K 35/744*      (2015.01)
*A61K 31/198*      (2006.01)
(Continued)

(52) U.S. Cl.
CPC .......... *A61K 35/744* (2013.01); *A61K 31/198* (2013.01); *A61K 36/48* (2013.01); *A61K 36/81* (2013.01); *A61P 37/04* (2018.01)

(58) Field of Classification Search
CPC ...... A61K 35/744; A61K 31/198; A61P 37/04
See application file for complete search history.

(56) References Cited

U.S. PATENT DOCUMENTS 8,771,675 B2    7/2014    Zink et al.
9,399,048 B2    7/2016    Tsai et al.
(Continued)

FOREIGN PATENT DOCUMENTS

DE    10206995 A1    9/2003
JP    S55102394 A    8/1980
(Continued)

OTHER PUBLICATIONS

Villageliu, Daniel, and Mark Lyte. "Dopamine production in Enterococcus faecium: a microbial endocrinology-based mechanism for the selection of probiotics based on neurochemical-producing potential." PLoS One 13.11 (2018) (Year: 2018).*

(Continued)

*Primary Examiner* — Louise W Humphrey
*Assistant Examiner* — Mary A Crum
(74) *Attorney, Agent, or Firm* — McKee, Voorhees & Sease, PLC

(57) ABSTRACT

Dopamine producing probiotics to increase immune responses to vaccination and to provide increased immune protection are provided. Also provided are dopamine producing synbiotic compositions, formulations, plants, and synthetic compounds, as well as methods for their use for targeted clinical and veterinary applications, for example, in promoting health and well-being and enhancing vaccine efficacy. Also provided is an approach for optimization of synbiotic delivery of a probiotic or other dopamine producing product with a dopamine precursor to beneficially aid in the use of such products for a variety of conditions and diseases, and particularly in the field of vaccines, whether prophylactic or therapeutic.

9 Claims, 16 Drawing Sheets

(51) Int. Cl.
    A61K 36/48    (2006.01)
    A61K 36/81    (2006.01)
    A61P 37/04    (2006.01)

(56) References Cited

U.S. PATENT DOCUMENTS

| | | | |
|---|---|---|---|
| 9,427,000 | B2 | 8/2016 | Boileau et al. |
| 9,580,680 | B2 | 2/2017 | Boileau et al. |
| 2006/0165822 | A1 | 7/2006 | Van Der Giessen et al. |
| 2007/0098744 | A1 | 5/2007 | Knorr et al. |
| 2008/0171106 | A1 | 7/2008 | Zink et al. |
| 2010/0068771 | A1 | 3/2010 | Schurmann et al. |
| 2014/0134689 | A1 | 5/2014 | Lee et al. |
| 2014/0301995 | A1 | 10/2014 | Mayra-Makinen et al. |
| 2015/0250833 | A1 | 9/2015 | Rubio Nistal et al. |
| 2016/0058808 | A1 | 3/2016 | Hsiao et al. |
| 2016/0129057 | A1 | 5/2016 | Jeon et al. |
| 2017/0184569 | A1 | 6/2017 | Keshavarzian et al. |
| 2017/0304376 | A1 | 10/2017 | Stromberg et al. |
| 2018/0251801 | A1 | 9/2018 | Aharoni et al. |
| 2019/0262298 | A1* | 8/2019 | Kanthasamy ........ A61K 31/198 |
| 2020/0297784 | A1 | 9/2020 | Lyte et al. |
| 2021/0138058 | A1 | 5/2021 | Mulder et al. |

FOREIGN PATENT DOCUMENTS

| | | | | |
|---|---|---|---|---|
| WO | WO-2008153655 | A2 * | 12/2008 | ............. A23K 10/18 |
| WO | WO-2019060661 | A1 * | 3/2019 | ............ A61K 31/198 |

OTHER PUBLICATIONS

Beirão, Breno CB, et al. "Effect of an Enterococcus faecium probiotic on specific IgA following live *Salmonella enteritidis* vaccination of layer chickens." Avian Pathology 47.3 (2018): 325-333 (Year: 2018).*
Feng, Yifei, and Yan Lu. "Immunomodulatory effects of dopamine in inflammatory diseases." Frontiers in immunology 12 (2021): 663102 (Year: 2021).*
Kasornpikul, Charunee, et al. "Efficacy of Isolated Probiotic Bacteria from Piglet Nostrils in Fattening Pigs." Silpakorn University Science and Technology Journal 10.3 (2016) (Year: 2016).*
Unban, Kridsada, et al. "Amylolytic enzymes acquired from L-lactic acid producing Enterococcus faecium K-1 and improvement of direct lactic acid production from cassava starch." Applied Biochemistry and Biotechnology 183 (2017): 155-170 (Year: 2017).*
Breitel et al., "Metabolic engineering of tomato fruit enriched in L-DOPA," Metabolic Engineering, May 2021, vol. 65, pp. 185-196.
Gerszberg et al., "Tomato (*Solanum lycopersicum* L.) in the service of biotechnology," Plant Cell Tissue Organ Culture, Mar. 2015, vol. 120, pp. 881-902.
Johnson et al., "Levodopa-Reduced Mucuna pruriens Seed Extract Shows Neuroprotective Effects against Parkinson's Disease in Murine Microglia and Human Neuroblastoma Cells, Caenorhabditis elegans, and Drosophila melanogaster," Nutrients, Aug. 2018, vol. 10, 14 pages.
Anderson et al., "Development of a Multienzyme Reactor for Dopamine Synthesis: II. Reactor Engineering and Simulation," Biotechnology and Bioengineering, vol. 40, 1992, pp. 388-395.
Barrett et al., "γ-Aminobutyric acid production by culturable bacteria from the human intestine," Journal of Applied Microbiology, vol. 113, 2012, pp. 411-417.
Derrien et al., "Mucin-bacterial interactions in the human oral cavity and digestive tract," Gut Microbes, vol. 1, Issue 4, 2010, pp. 254-268.
EFSA Panel, "Scientific Opinion on the safety and efficacy of Oralin® (Enterococcus faecium) as a feed additive for calves for rearing, piglets, chickens for fattening, turkeys for fattening and dogs," EFSA Journal, vol. 12, Issue 6, 2014, 19 pages.
Galland, L., "The Gut Microbiome and the Brain," Journal of Medicinal Food, vol. 17, Issue 12, 2014, pp. 1261-1272.
Gibson et al., "Use of a three-stage continuous culture system to study the effect of mucin on dissimilatory sulfate reduction and methanogenesis by mixed populations of human gut bacteria," Applied and Environmental Microbiology, vol. 54, No. 11, Nov. 1988, pp. 2750-2755.
Hemarajata et al., "Effects of probiotics on gut microbiota: mechanisms of intestinal immunomodulation and neuromodulation," Therapeutic Advances in Gastroenterology, vol. 6, Issue 1, 2013, pp. 39-51.
Lam et al., "Comparative analysis of the complete genome of an epidemic hospital sequence type 203 clone of vancomycin-resistant Enterococcus faecium," BMC Genomics, vol. 14, No. 595, 2013, 15 pages.
Leung et al., "Effects of porphyrins and inorganic iron on the growth of Prevotella intermedia," FEMS Microbiology Letters, vol. 209, Issue 1, 2002, pp. 15-21.
List of dopaminergic drugs, Wikipedia, [retrieved on Nov. 15, 2018]. Retrieved from the Internet: <URL: https://en.wikipedia.org/wiki/List_of_dopaminergic_drugs>, 5 pages.
Lyte, M., "Probiotics function mechanistically as delivery vehicles for neuroactive compounds: Microbial endocrinology in the design and use of probiotics," Bioessays, vol. 33, 2011, pp. 574-581.
Mackie et al., "InfoGest Consensus Method," In: The Impact of Food Bioactives on Health: in vitro and ex vivo models, Chapter 2, Springer, New York, 2015, pp. 13-22.
Marques et al., "Simulated Biological Fluids with Possible Application in Dissolution Testing," Dissolution Technologies, vol. 18, Aug. 2011, pp. 15-28.
PET System Manual, Novagen, TB055 8th Edition, Feb. 1999, 49 pages.
Ramya et al., "Herbs containing L- Dopa: An update," Ancient Science of Life, vol. 27, 2007, pp. 50-55.
Sarkar et al., "Psychobiotics and the Manipulation of Bacteria—Gut—Brain Signals," Trends in Neurosciences, vol. 39, No. 11, Nov. 2016, pp. 763-781.
Van Kessel et al., "Gut bacterial tyrosine decarboxylases restrict levels of levodopa in the treatment of Parkinson's disease," Preprint, Nature Communications, vol. 10, No. 310, 2019, 50 pages.
Villageliu et al., "A microbial endocrinology-based simulated small intestinal medium for the evaluation of neurochemical production by gut microbiota," FEMS Microbiology Ecology, vol. 94, No. 7, 2018, 9 pages.
Villageliu et al., "Dopamine production in Enterococcus faecium: a microbial endocrinology-based mechanism by which probiotics may influence host physiology," Manuscript Draft, PLOS One, vol. 13, 2018, 17 pages.
Vimont et al., "Bacteriocin-Producing Enterococcus faecium LCW 44: A High Potential Probiotic Candidate from Raw Camel Milk," Frontiers in Microbiology, vol. 8, Article 865, May 2017, 12 pages.
Wolken et al., "The mechanism of the tyrosine transporter TyrP supports a proton motive tyrosine decarboxylation pathway in Lactobacillus brevis," Journal of Bacteriology, vol. 188, No. 6, Mar. 2006, pp. 2198-2206.
Yang et al., "Mode of Action of the TyrR Protein: Repression and Activation of the tyrP Promoter of *Escherichia coli*," Molecular Microbiology, vol. 52, Issue 1, Apr. 2004, pp. 243-256.
Zhao et al., "Biosynthesis of Tyramine with Permeabilized Recombinant *Escherida coli* Cells Expressing Tyrosine Decarboxylase," Journal of Chemical Engineering of Chinese Universities, vol. 31, No. 6, Dec. 2017, 16 pages.
Zhu et al., "Crystal structure of tyrosine decarboxylase and identification of key residues involved in conformational swing and substrate binding," Scientific Reports, vol. 6, No. 27779, 2016, 10 pages.
Zimmerman et al., "The influence of probiotics on vaccine responses—A systematic review", Vaccine, vol. 36, pp. 207-213, 2018.

* cited by examiner

USE OF DOPAMINE PRODUCING PRODUCTS TO INCREASE VACCINE EFFICACY

CROSS REFERENCE TO RELATED APPLICATIONS

This application claims priority under 35 U.S.C. § 119 to provisional patent application U.S. Ser. No. 63/262,301, filed Oct. 8, 2021. The provisional patent application is herein incorporated by reference in its entirety, including without limitation, the specification, claims, and abstract, as well as any figures, tables, appendices, or drawings thereof.

TECHNICAL FIELD

The present disclosure is directed to dopamine producing probiotics to increase immune response to vaccination and to provide increased protection. The present disclosure is further directed to dopamine producing synbiotic compositions, formulations, plants, and synthetic compounds and their use for targeted clinical and veterinary applications, for example, in promoting health and well-being and/or treating therapeutic conditions. Also disclosed is the use of dopamine generated in fermenters in vitro that is administered into animal feed by encapsulation and other means.

BACKGROUND

A major cause of economic losses in the U.S. economy are illnesses resulting from the infection of humans, farm animals, and aquatic invertebrates with disease-causing agents. Infections can be caused by a wide range of pathogens, including bacteria, viruses, fungus and parasites. Porcine reproductive respiratory syndrome virus (PRRSV), *Salmonella* bacteria, and Malaria (i.e., *Plasmodium vivax* or *P. falciparum*) are three of the most economically significant pathogens worldwide, motivating worldwide vaccine development efforts. The prevalence of these and other pathogens has also motivated the development of adjuvants, immunostimulatory molecules, and other products that enhance the efficacy of such vaccines. Notably, the ability of natural or synthetic sources of dopamine to modify the response to vaccinations has come of interest within the last decade.

Probiotics are designated as living microorganisms that may be used for both maintenance of health as well as treatment of specific clinical conditions ranging from gastrointestinal infection to the treatment of neuropsychiatric-related behavioral issues. Probiotics are also extensively used in the farm production industry (chickens, pigs and cattle), aquaculture, as well as in the treatment of companion animals (dogs, cats, horses). Similarly, probiotics are also extensively used in humans to treat gastrointestinal inflammation and associated conditions negatively impacting the well-being of humans. A critical impediment to the more widespread use of probiotics from *Enterococcus* spp. such as *Enterococcus faecium* (referred to hereafter as, "*E. faecium*") is the lack of understanding of the mechanism(s) by which they may exert their purported benefits. By not understanding the mechanism it then becomes nearly impossible to screen the large libraries of probiotics that exist to identify those strains which may be of benefit. Notably *E. faecium* has been found to have the capacity to produce dopamine along with all of members of the genus *Enterococcus*. Relatedly, the disclosure of the present application provides a screening approach based upon a microbial endocrinology concept which the inventor has pioneered in the scientific literature.

Dopamine has a variety of uses. For example, dopamine has been used to treat issues, and associated symptoms, including, but not limited to, depression, the immune response, inflammation, gastric ulcers, and is used as an intermediate for other neurochemicals. Further, dopamine can serve as a potent regulator of the immune system. For example, dopamine has been shown to exert a protective effect against the development of inflammation in model systems such as that in mouse colitis. Herak-Perkovic V, et al. *J Vet Pharmacol Ther.* 2001; 24(4):267-73. Of particular note is a study in zebrafish which was used as a whole animal model with which to evaluate over 1500 compounds as possible therapeutic agents to reduce neutrophilic infiltration as part of the inflammatory pathogenesis in the gut. Oehlers S H, et al. *FEBS J.* 2017; 284(3):402-13. Of all the compound classes studied, dopamine receptor agonists were consistently shown to be superior to nearly all other compounds in their ability to suppress the development of inflammation. Conversely, dopamine receptor antagonists which effectively block dopamine binding within the gut permitted increased neutrophilic inflammation within the gut which resulted in a worsened degree of inflammation.

Notably, dopamine is quickly absorbed in the upper intestinal tract as well as subject to degradation by neuronal, immune and nonimmune cells thereby reducing its efficacy when administered as a pill or other one-time dosing. As a result, the vast majority of studies, which have sought to utilize dopamine to treat disease have utilized dopamine receptor agonist drugs. Further, because dopamine is highly prone to oxidation, it is not well-suited for incorporation into feed. Thus, a means whereby dopamine is delivered in situ in a constant defined amount to influence immune responsiveness is needed. In this regard, the dopamine-producing probiotic satisfies that crucial requirement.

SUMMARY

Methods of enhancing the immune response to a vaccine in a subject are provided. In some embodiments, the method comprises administration of a therapeutically effective amount of at least one dopamine producing probiotic to the subject. In some embodiments, the dopamine producing probiotic is a bacterial strain, such as a bacteria of the genus *Enterococcus* or *Vagococcus*. In some embodiments, the dopamine producing probiotic is administered with a therapeutically effective amount of dopamine precursor, L-3,4-dihydroxyphenylalanine (L-dopa).

Compositions comprising a therapeutically effective amount of at least one dopamine producing probiotic, a therapeutically effective amount of an L-dopa producing plant or extract thereof, and optionally, a therapeutically effective amount of a co-factor of dopamine are also provided. In some embodiments, the L-dopa producing plant is *Vicia faba* or *Mucuna pruriens*. In some embodiments, the therapeutically effective amount of the L-dopa producing plant is provided in an amount from about 0.1 mg L-dopa/kg animal feed to about 10 g L-dopa/kg animal feed. In some embodiments, the co-factor of dopamine is pyridoxal phosphate.

Methods for treating and/or preventing inflammation in a subject are also provided. In some embodiments, the method comprises administering a therapeutically effective amount of at least one dopamine producing probiotic to the subject.

In some embodiments, the dopamine producing probiotic is administered with a therapeutically effective amount of L-dopa.

These and/or other objects, features, advantages, aspects, and/or embodiments will become apparent to those skilled in the art after reviewing the following brief and detailed descriptions of the drawings. Furthermore, the present disclosure encompasses aspects and/or embodiments not expressly disclosed but which can be understood from a reading of the present disclosure, including at least: (a) combinations of disclosed aspects and/or embodiments and/or (b) reasonable modifications not shown or described.

BRIEF DESCRIPTION OF THE DRAWINGS

The following drawings form part of the specification and are included to further demonstrate certain embodiments or various aspects of the disclosure. In some instances, embodiments of the disclosure can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIG. 2A shows L-dopa added to growth medium in the absence of E. faecium, exhibiting the presence of an L-dopa peak and no constitutive dopamine according to embodiments of the invention. FIG. 2B shows substantial but not complete enzymatic conversion of L-dopa to dopamine after overnight incubation in L-dopa containing medium with an E. faecium isolate according to embodiments of the invention. FIG. 2C shows complete conversion of all L-dopa to dopamine with another E. faecium isolate demonstrating the need to screen candidate E. faecium isolates for use according to embodiments of the invention.

FIGS. 9A and 9B shows that chickens fed a diet supplemented with higher concentrations of E. faecium plus L-dopa (Group 4) had a significantly increased level of dopamine in the cecal tissue (FIG. 9A) and cecal contents (FIG. 9B) compared to non-supplemented chickens (Groups 1 and 2) and chickens supplemented with a lower concentration of E. faecium plus L-dopa (Group 3). FIGS. 9C and 9D shows that chickens fed a diet supplemented with E. faecium plus L-dopa (Groups 3 and 4) had a significantly increased level of dopamine metabolite 3-methoxytyramine in the cecal tissue (FIG. 9C) and cecal contents (FIG. 9D) compared to non-supplemented chickens (Groups 1 and 2). FIG. 9E presents the levels of S. enteritidis (CFU/g) present in the cecal contents of supplemented and non-supplemented chickens and shows that chickens fed a diet supplemented with E. faecium plus L-dopa (Groups 3 and 4) demonstrated a significantly increased ability to retard growth and colonization following an infectious challenge of S. enteritidis as compared to non-supplemented chickens (Groups 1 and 2).

Figure 1:
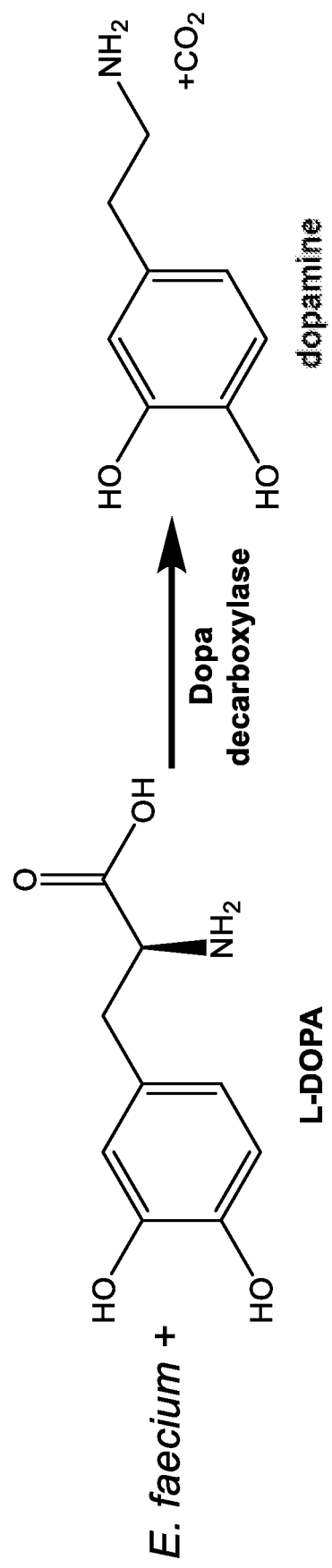
FIG. 1 shows the production of dopamine via decarboxylation of the precursor molecule L-3,4-dihydroxyphenylalanine (hereafter, "L-dopa") according to embodiments of the invention.

Reference to various embodiments does not limit the scope of the disclosure. Figures represented herein are not limitations to the various embodiments according to the disclosure and are presented for exemplary illustration of the disclosure.

DETAILED DESCRIPTION

The present disclosure relates to the use of dopamine producing probiotics, plants, and chemicals (i.e., non-biologically produced dopamine) to improve vaccine efficacy in a range of animal species. The range of subject animal species is very broad, including humans, domesticated animals, farm animals, aquatic animals, avian animals, and any other species of animal that is regularly vaccinated. In an example, farm animals may include cattle, swine, sheep, horses, goats, llamas, alpacas, donkeys, rabbits, and dairy cows. In an example, aquatic animals may include both vertebrates and invertebrates, including, but not limited to, fish, shrimp, prawns, lobster, octopus, oysters, crabs, squid, and mollusks. In an example, avian animals that may benefit from improved vaccine response with the present invention include hens, chickens, turkeys, ducks, ducklings, geese, goslings, guinea fowls, pheasants, bantams, quails, and pigeons. A range of other farm animals and aquaculture animals are contemplated.

Similarly, the present disclosure is applicable to a wide array of vaccines encompassing viral, bacterial, parasitic (i.e., malaria) and fungal species. In an example, the present disclosure may be applicable to vaccines commonly administered to farm animals, such as the vaccine for porcine reproductive respiratory syndrome virus (PRRSV). In a further example, the present disclosure may be applicable to live aquaculture vaccines such as the *Arthrobacter* vaccine against bacterial kidney disease (BKD) for use in salmonids, the *Edwardsiella ictaluri* (hereafter, "*E. ictaluri*") vaccine against enteric septicemia of catfish (ESC), and the *Flavobacterium columnare* vaccine against columnaris in catfish. Similarly, the present disclosure may be applicable to a live viral hemorrhagic septicemia virus (VHSV) vaccine and a live viral vaccine against Koi herpesvirus (KHV) for carp.

In another instance, the present disclosure may be applicable to vaccines protective against salmonellosis caused by different *Salmonella* bacteria, including *Salmonella enterica* subspecies *enterica* serovar Paratyphi C (*Salmonella* Paratyphi C), *Salmonella enterica* subspecies *enterica* serovar Infantis (*Salmonella* Infantis), *Salmonella enterica* subspecies *enterica* serovar Mbandaka (*Salmonella* Mbandaka), *Salmonella enterica* subspecies *enterica* serovar Livingstone (*Salmonella* Livingstone), *Salmonella enterica* subspecies *enterica* serovar Virchow (*Salmonella* Virchow), *Salmonella enterica* subspecies *enterica* serovar Ohio (*Salmonella* Ohio), *Salmonella enterica* subspecies *enterica* serovar Montevideo (*Salmonella* Montevideo), *Salmonella enterica* subspecies *enterica* serovar Tennessee (*Salmonella* Tennessee), *Salmonella enterica* subspecies *enterica* serovar Rissen (*Salmonella* Rissen), *Salmonella enterica* subspecies *enterica* serovar Decatur (*Salmonella* Decatur), *Salmonella enterica* subspecies *enterica* serovar Bareilly (*Salmonella* Bareilly), *Salmonella enterica* subspecies *enterica* serovar Menston (*Salmonella* Menston), *Salmonella enterica* subspecies *enterica* serovar Oranienburg (*Salmonella* Oranienburg), and *Salmonella enterica* subspecies *enterica* serovar Thompson (*Salmonella* Thompson).

In another example, the present disclosure may be applicable to vaccines protective against infection with *Campylobacter* bacteria, including *Campylobacter jejuni* and *Campylobacter coli*. In some embodiments, the vaccine may be administered to poultry to decrease poultry intestinal *Campylobacter* load and thus decrease the risk of human campylobacteriosis following the consumption of infected poultry.

In a further example, the present disclosure may be applicable to vaccines administered to poultry, including broiler chickens and turkey, to provide protection from necrotic enteritis caused by *Clostridium perfringens* or coccidiosis caused by the protozoa *Eimeria*, including *Eimeria acervulina, Eimeria brunetti, Eimeria maxima, Eimeria mitis, Eimeria tenella*, and/or *Eimeria necatrix*.

The present disclosure may also be applicable to commonly administered human vaccines, including, but not limited to, oral vaccines, such as those protective against rotavirus, adenovirus, cholera, and typhoid fever, intramuscular vaccines, such as those protective against diphtheria, tetanus, whooping cough (pertussis), pneumococcal pneumonia, meningitis, and hepatitis, and intranasal vaccines, such as the live attenuated influenza vaccine.

All members of the *Enterococcus* genus have been found to have the capacity to produce dopamine in the presence of L-dopa. Thus, while *E. faecium* has been found to have the capacity to produce dopamine, and thereby enhance vaccine efficacy across many species, the capacity to produce dopamine is not limited solely to *E. faecium*. In addition, it is possible that other species of bacteria belonging to other non-Enterococcal genera may produce dopamine, and that genetically modified organisms may be engineered to produce dopamine. For example, it is increasingly recognized that the gut microbiota has a number of built-in redundancies. Using the teachings of the present disclosure, it would be within the capability of one having ordinary skill in the art to find other genera capable of producing dopamine. Accordingly, although *E. faecium* is the bacterium used in some embodiments of the present disclosure, the disclosure is not limited to same.

It is further contemplated that a subject may be fed a non-GMO L-dopa producing plant or other food at a significant enough volume that a therapeutic effect is achieved. In some embodiments, the L-dopa producing plant produces low concentrations of L-dopa. Notably, in some embodiments, the L-dopa producing plant includes *Mucuna pruriens* and/or *Vicia faba*.

It is further contemplated that a subject may be fed an L-dopa producing plant which has been genetically engineered to produce L-dopa. In some embodiments, the L-dopa producing plant may be a *Solanum lycopersicum* (tomato) plant, which has been previously successfully genetically modified to produce increased levels of L-dopa. In other embodiments, the L-dopa producing plant may be a plant of the genus *Nicotiana*.

In one example, the present application discloses use of a bacteria of genus *Enterococcus*, which is shown to improve the efficacy of porcine reproductive respiratory syndrome virus (PRRSV) vaccination resulting in reduced PRRS V-related disease. This finding is consistent with studies demonstrating that key immune regulatory cells within the gut and lung possess dopamine receptors which can modulate immune cellular function and thereby regulate the immune response to vaccination. In addition, direct modulation of the immune system by the neurotransmitter dopamine through autocrine/paracrine manner has been suggested. For example, dopamine can potentiate the production of Th2 cytokines by human naïve CD4 T-cells, of Th1 cytokines by activated CD4 T-cells; or of Th17 cytokines (IL-23) by DCs, thereby potentially enhancing immune response to vaccination.

In some embodiments, the present disclosure describes the ability of dopamine sources such as *E. faecium* and other members of the genus *Enterococcus* to increase dopamine in animals and increase the immunological responsiveness in pigs to PRRSV vaccination. In other embodiments, the present disclosure describes the ability of *Enterococcus*-provided-dopamine to protect against PRRSV challenge, demonstrating that there may be a cellular and humoral immune response to PRRSV vaccination. In some embodiments, in-situ delivery of consistent levels of dopamine to tissue sites may induce a robust response to PRRSV vaccination. The finding that dopamine-containing products can increase levels of dopamine in the gut intraluminal and thereby elevate levels of dopamine within the lung provides a means to deliver dopamine to increase the strength of vaccine response.

In one embodiment, the present disclosure contemplates the use of a dopamine producing probiotic, a bacteria of genus *Enterococcus*, or another dopamine producing product, to improve the efficacy of *Salmonella* vaccines (including attenuated and inactivated vaccines) resulting in reduced *Salmonella*-related disease. Notably, *Salmonella*-related disease has witnessed a rapid spread through the animal production systems at a global level and is particularly important to poultry production.

In another embodiment, the present disclosure contemplates the use of a dopamine producing probiotic, a bacteria of genus *Enterococcus*, or another dopamine producing product, to improve the efficacy of PRRSV vaccination resulting in reduced PRRSV-related disease. Numerous studies have demonstrated that key immune regulatory cells within the gut and lung possess dopamine receptors which can modulate immune cellular function and thereby regulate the response to vaccination. The in-situ delivery of consistent levels of dopamine to tissue sites where a robust response to PRRSV vaccination occurs is not currently possible due to the labile nature of dopamine. The present disclosure describes a dopamine-producing probiotic that can increase the gut intraluminal dopamine levels resulting in elevated levels of dopamine within the lung providing a means to deliver dopamine to increase the strength of the vaccine response.

In some embodiments, oral administration of a bacteria of genus *Enterococcus* results in the intraluminal production of dopamine within the gut as well as increased tissue concentrations in the lung. The present disclosure therefore provides: (1) the determination the dose-response kinetics of *Enterococcus* produced dopamine on the dopamine concentrations and immunological responsiveness in piglets fed dopamine producing *Enterococcus* for 28 days following weaning and (2) examines the ability of dopamine producing *Enterococcus* to enhance the efficacy of PRRSV vaccine to protect pigs fed *Enterococcus* for 28 days following weaning against PRRSV challenge. Critically, this mechanistically driven application targets a known pathway of action that is recognized to play a pivotal role in the regulation of immune responsiveness.

In a preferred embodiment, administration of the immune-modulating neurochemical dopamine prior to and at the time of PRRSV vaccination increases host response to the vaccine leading to increased neutralizing antibody production and a more effective cell mediated response and hence increased protection against PRRSV infection. The continuous delivery of dopamine is achieved through the use of the probiotic, a bacteria of genus *Enterococcus*, which is approved for use in pigs and which is capable of the in-situ production of dopamine. The present disclosure demonstrates that a dopamine producing probiotic can increase the immunological response to PRRSV vaccination and thereby provide greater protection in the face of subsequent PRRSV challenge. This inexpensive means of increasing PRRSV vaccine efficacy will provide immediate benefits to the pig production industry.

The present disclosure further relates to methods for selecting or identifying probiotic strains, plants, and small molecule compounds capable of producing neurochemicals in the gut of an animal or human.

The present disclosure further relates to methods for treating a subject with a recent vaccination and/or need for gut health with a probiotic strain capable of producing neurochemicals in the gut of the subject. Notably, the present disclosure also relates to methods for treatment of behavior. Still further the present disclosure relates to synbiotic compositions providing for administration to a vaccinated subject comprising a therapeutically effective amount of at least one probiotic strain; and a therapeutically effective amount of a precursor of dopamine. The present methods and compositions have many advantages over conventional administration and/or screening of probiotic strains, plants, and small molecule compounds. Without being limited to the particular mechanisms and benefits of the disclosure, the methods and compositions described provide the inventor the ability to select and use natural or synthetic sources of dopamine in medicine based on a desirable mechanism of action, namely a microbial endocrinology-based mechanism for probiotic strains, plants, and small molecule compounds to exert their purported benefits.

The present disclosure further relates to low-cost fermentation culture or minimal media which includes a L-dopa source and a fermented plant substrate, such as Distiller's dried grains with solubles (DDGs). The present disclosure further relates to methods of culturing bacteria capable of producing dopamine in the presence of L-dopa under anaerobic or aerobic fermentation conditions. The present methods and compositions have many advantages over conventional dopamine production. Without being limited to the particular mechanisms and benefits of the invention, the methods and compositions overcome a lack of knowledge in ability to produce dopamine using low-cost inputs on an industrial level. The present disclosure overcomes these limitations and provides methods for the use of bacteria to produce dopamine using low-cost media.

The embodiments of this disclosure are not limited to particular compositions or methods of production, which can vary and may be understood by skilled artisans. It is further to be understood that all terminology used herein is for the purpose of describing particular embodiments only and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers defining the range and include each integer within the defined range. Throughout this disclosure, various aspects of this disclosure are presented in a range format. It should be understood that the description in range format is merely for convenience and brevity and should not be construed as an inflexible limitation on the scope of the disclosure. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 1½, and 4¾. This applies regardless of the breadth of the range.

The phrase "and/or," when used between elements in a list, is intended to mean either (1) that only a single listed element is present, or (2) that more than one element of the list is present. For example, "A, B, and/or C" indicates that the selection may be A alone; B alone; C alone; A and B; A and C; B and C; or A, B, and C. The phrase "and/or" may be used interchangeably with "at least one of" or "one or more of" the elements in a list.

So that the present disclosure may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present disclosure, the following terminology will be used in accordance with the definitions set out below.

The term "about," as used herein, refers to variation in the numerical quantity that can occur, for example, through typical measuring techniques and equipment, with respect to any quantifiable variable, including, but not limited to, mass, volume, time, distance, and the like. Further, given solid and liquid handling procedures used in the real world, there is certain inadvertent error and variation that is likely through differences in the manufacture, source, or purity of the ingredients used to make the compositions or carry out the methods and the like. The term "about" also encompasses amounts that differ due to different equilibrium conditions for a composition resulting from a particular initial mixture. The term "about" also encompasses these variations. Whether or not modified by the term "about," the claims include equivalents to the quantities.

As used herein, the "alimentary tract" refers to the pathway by which food enters the body of a subject and solid wastes are expelled. The alimentary canal includes, for example, the mouth, pharynx, esophagus, stomach, small intestine, large intestine, and anus.

The phrase "and/or," when used between elements in a list, is intended to mean either (1) that only a single listed element is present, or (2) that more than one element of the list is present. For example, "A, B, and/or C" indicates that the selection may be A alone; B alone; C alone; A and B; A and C; B and C; or A, B, and C. The phrase "and/or" may be used interchangeably with "at least one of" or "one or more of" the elements in a list.

As used herein, an "effective amount" or "therapeutically effective amount" refers to the amount of a compound, such as a probiotic strain and/or precursor material that is sufficient to prevent, treat, reduce and/or ameliorate the symptoms and/or underlying causes of a disorder or disease. In an exemplary aspect, an "effective amount" or "therapeutically effective amount" refers to the amount of probiotic and/or precursor that is sufficient to prevent, inhibit, and/or treat a recent vaccination and/or promoting health in the gut of an animal or human.

Also, as used herein, the term "gut" refers to the gastrointestinal tract as well as liver, spleen, pancreas, and other organs served by the blood supply to and from the gut.

The term "intestinal microbiota", as used herein, refers to the population of microorganisms inhabiting the gastrointestinal tract. The term was previously referred to as the intestinal flora.

The term "microbiome", as used herein, refers to a population of microorganisms from a particular environment, including the environment of the body or a part of the body. The term is interchangeably used to address the population of microorganisms itself (sometimes referred to as the microbiota), as well as the collective genomes of the microorganisms that reside in the particular environment. The term "environment", as used herein, refers to all surrounding circumstances, conditions, or influences to which a population of microorganisms is exposed. The term is intended to include environments in a subject, such as a human and/or animal subject.

"Microorganism" refers to an organism or microbe of microscopic, submicroscopic, or ultramicroscopic size that typically consists of a single cell. Examples of microorganisms include bacteria, viruses, parasites, fungi, certain algae, and protozoa. The term "microbial" indicates pertaining to, or characteristic of a microorganism.

As used herein, the term "neurochemical" refers to small organic molecules and peptides that participate in neural, immune and other general physiological activities. Neurochemicals can be produced within in various parts of a subject, such as the gut, brain, etc. Such biogenic neurochemicals are capable of eliciting neural activity. Exemplary neurochemicals include both neurotransmitters and neuromodulators, which can be either excitatory or inhibitor in nature. Exemplary neurochemicals include catecholamines. Further exemplary neurochemicals include glutamate, dopamine, serotonin, histamine, norepinephrine, epinephrine, phenethylamines, thyronamine compounds, tryptamine, GABA, acetylcholine, and the like.

"Non-pathogenic bacteria" refer to bacteria that are not capable of causing disease or harmful responses in a host. In some embodiments, non-pathogenic bacteria are commensal bacteria. Examples of non-pathogenic bacteria include, but are not limited to *Bacillus* spp., *Bacteroides* spp., *Bifidobacterium* spp., *Brevibacterium* spp., *Clostridium* spp., *Enterococcus* spp., *Escherichia coli*, *Lactobacillus* spp., *Lactococcus* spp., *Saccharomyces* spp., and *Staphylococcus* spp. Naturally pathogenic bacteria may be genetically engineered to provide reduce or eliminate pathogenicity according to standard methods in the art.

The term "population", as used herein, refers to a plurality of individual organisms, in the context of this invention, the term refers in particular to a collection of organisms of divers taxonomic affiliation, in particular bacteria.

"Prebiotic" is used to refer to a food or dietary supplement that confers a health benefit on a subject associated with modulating a microbiota. Prebiotics do not need to be drugs, and in most instances, are not drugs, not functioning because of absorption of the component, not due to the component acting directly on the subject, and are due to changes to the resident bacteria—either changing the proportions of the resident bacteria or the activities thereof. As referred to herein, a prebiotic includes a precursor and/or co-factor to a neurochemical for combined use with a probiotic. For example, a prebiotic according to the present disclosure may be L-dopa.

"Probiotic" is used to refer to live, non-pathogenic microorganisms, e.g., bacteria, which can confer health benefits to a host organism that contains an appropriate amount of the microorganism. In some embodiments, the host organism is a mammal. In some embodiments, the host organism is a human. Some species, strains, and/or subtypes of non-pathogenic bacteria and yeast are currently recognized as natural or synthetic sources of dopamine. Examples of probiotics include, but are not limited to, *Candida* spp., *Debaryomyces* spp., *Debaryomyces* spp., *Enterococcus* spp., *Kluyveromyces* spp., *Kluyveromyces* spp., *Saccharomyces* spp., *Yarrowia* spp., Bifidobacteria spp., *Escherichia coli*, *Vagococcus* spp., *Carnobacterium* spp., *Melissococcus* spp. and *Lactobacillus* spp., e.g., *Candida humilis, Debaryomyces hansenii, Debaryomyces occidentalis, Kluyveromyces lactis, Kluyveromyces lodderae, Kluyveromyces marxianus, Saccharomyces cerevisiae, Saccharomyces boulardii, Yarrowia lipolytica, Bifidobacterium bifidum, Enterococcus faecium, Enterococcus faecalis, Enterococcus hirae, Enterococcus casseliflavus, Enterococcus gallinarum, Escherichia coli* strain Nissle, *Lactobacillus acidophilus, Lactobacillus bulgaricus, Lactobacillus paracasei, Lactobacillus plantarum, Vagococcus fluvaialis*. The probiotic may be a variant or a mutant strain of bacterium.

Non-pathogenic bacteria may be genetically engineered to enhance or improve desired biological properties, e.g., survivability. Non-pathogenic bacteria may be genetically engineered to provide probiotic properties. Probiotic bacteria and/or yeast may be genetically engineered to enhance or improve probiotic properties. Without being limited to a particular mechanism of the disclosure, probiotics differ in their ability to produce neurochemicals in the gut of a subject and therefore have differing abilities to treat a subject according to the methods disclosed herein.

The terms "immune response" or "vaccination response", as used herein, are intended to mean that the host subject mounts an active immune response to a vaccine such that upon subsequent exposure to the disease-causing agent, the subject is able to combat the infection. Thus, an immune response will decrease the incidence of morbidity and mortality from subsequent exposure to the disease-causing agent among host subjects. Those skilled in the art will understand that the production of a protective immune response may be assessed by evaluating the effects of vaccination on a population as a whole, e.g., there may still be morbidity and mortality in a minority of vaccinated subjects. Furthermore, protection also includes a lessening in severity of any gross or histopathological changes and/or of symptoms of the disease, as compared to those changes or symptoms typically caused by the isolate in similar subjects which are unprotected (i.e., relative to an appropriate control). Thus, a protective immune response will decrease the symptoms of the disease, which will vary according to the disease. Disease morbidity and/or mortality are reduced and where there also may be a reduced titer of infection upon exposure to the disease-causing agent. In some embodiments, immune response is measured by serum viremia, seroconversion, and neutralizing antibodies, by immunohistochemistry, or by any other titer methods known in the art.

The terms "enhanced immune response" or "enhanced vaccination response", as used herein, are intended to mean that the host subject mounts a stronger active immune response to a vaccine when the vaccine is administered in conjunction with a dopamine producing probiotic, as compared to a similar subject administered the same vaccine without the dopamine producing probiotic. An enhanced immune response may be measured by increased production of antibodies against the infectious agents. An enhanced immune response may also be measured by increased levels of cells associated with immune responses, including T cells, T helper ($T_h$) cells, macrophages, and B cells.

The term "L-dopa" refers to Levodopa (also known as 3,4-dihydroxy-L-phenylalanine), an amino acid precursor of dopamine. L-dopa is converted to dopamine by DOPA decarboxylase in human and animal species and can cross the blood-brain barrier. When in the brain, L-dopa is decarboxylated to dopamine and stimulates the dopaminergic receptors, thereby increasing the supply of endogenous dopamine to a subject. L-DOPA is also produced as a drug to treat Parkinson's disease.

The term "sample", as used herein, refers to any sample suitable for analyzing or typing according to the methods of the present invention. A sample may be collected from an organism (e.g., human or other mammal subject) and can be in any form, including without limitation a solid material such as a tissue, cells, a cell pellet, a cell extract, or a biopsy, or a biological fluid such as urine, blood, stool, saliva, amniotic fluid, exudate from a region of infection or inflammation, or the like.

As used herein, a "subject" includes an animal species, including humans, domesticated animals, farm animals, aquatic animals, avian animals, and any other species of animal that is regularly vaccinated. A non-limiting list may include domestic animals such as dogs, cats, guinea pigs, rabbits, hamsters, gerbils, mice, and rats; farm animals such as cattle, swine, sheep, horses, goats, llamas, alpacas, and donkeys; aquatic animals such as finfish, shrimp, prawns, lobster, octopus, oysters, crabs, squid, and mollusks; and avian animals such as hens, chickens, turkeys, ducks, ducklings, geese, goslings, guinea fowls, pheasants, bantams, quails, and pigeons.

The term "synbiotic" or "synbiotic composition", as used herein, refers to combining probiotics and prebiotics in a form of synergism. In a particular aspect, the prebiotics include neurochemicals and its precursors and/or co-factors to be utilized by the probiotic of the synbiotic composition. A synbiotic composition can include a co-formulated composition containing both components and additional functional ingredients required for the delivery thereof. More generally, a synbiotic treatment or method is provided by the delivery of both probiotics and prebiotics to a subject in need thereof, regardless of whether the components are delivered separately to the subject.

The term "culture media" may refer to a growth media which may contain all the elements that most bacteria need for growth and are not selective, so they are used for the general cultivation and maintenance of bacteria. Culture media may be either an "undefined media" or a "defined media." An undefined media contains a carbon source, such as but not limited to glucose, water, various salts, and a source of amino acids and nitrogen arising from extracts of yeast, animals, or plants with undefined compounds. A defined media is when all the chemicals used are known and does not contain any yeast, animal, or plant tissues. The media may contain additional supplements, buffers, enzymatic cofactors, and minerals depending on the needs of the strain of bacteria. For example, the media may be supplemented with a source of L-dopa for the production of dopamine.

The term "minimal media" or "minimalist media" as used herein may refer to a growth media which contains the minimal amounts of compounds and nutrients to support growth and produce industrially viable quantities of dopamine. Minimal media may contain a carbon source, such as glucose or less energy rich source such as succinate, various salts, water and minimal amounts of supplements which may be required for the production of dopamine. For example, the media may be supplements with DGGs. The media may contain additional supplements, buffers, enzymatic cofactors, and minerals depending on the needs of the strain of bacteria. For example, the media may be supplemented with a source of L-dopa for the production of dopamine. Supplements may be either purified or in a raw or course form.

The present disclosure provides, inter alia, compositions and methods for the production of dopamine. The compositions and methods of the invention function to produce dopamine at industrial levels at lower costs than conventional methods. The media may accomplish the low costs effects by reducing the reliance on expensive, purified sources of nitrogen and carbon sources.

Production of Dopamine

In an embodiment, dopamine is produced by a cell comprising of an aromatic decarboxylase which is capable of decarboxylating L-dopa into dopamine. Strains of bacteria may be screened for the presence of aromatic decarboxylase or bacteria may be transformed with an aromatic decarboxylase using standard techniques. Bacteria with an aromatic decarboxylase may then be cultured in a fermentation media supplemented with L-dopa. After about 2, about 3, about 4, about 6, about 8, about 10, about 12, about 16, about 24 hours, about 48, about 72 hours, about 1 week, about 2 weeks, or for as long as the culture or retained dopamine remains viable, the dopamine may then be purified from the media. In a preferred embodiment, dopamine is purified from about 24 to 72 hours after culture. In a preferred embodiment, the cell is a member of the genus *Enterococcus* or *Vagococcus*.

In a further embodiment, the transfected or transformed cell may be either a prokaryote or eukaryote cell. For example, the cell may be bacterial, fungus, insect, plant, animal, or human. By way of a non-limiting example, a cell exhibiting robust growth in the low-cost fermentation media may be transformed or transfected such that said cell has increased or is conferred dopamine production.

In another embodiment, a transfected or transformed cell with aromatic decarboxylase may be stacked with a catecholamine transporter. This may allow a cell increased dopamine production due to an increased ability to both uptake and then process L-dopa into dopamine. Cells may also be cultured in a bioreactor. The term "bioreactor" refers to any manufactured or engineered device or system that supports a biologically active environment. By way of nonlimiting example, a bioreactor may be a single-use or multi-use flask, roller bottle, tank, vessel, or other container which may support the growth of a cell culture. The bioreactor may comprise of an agitator, baffle, sparger, and/or a jacket. The bioreactor may be an open or closed system. An open system may allow the culture to be fed a continuous or intermittent supply of L-dopa. The cells may be fixed to a substrate within the bioreactor or adhered to the inner surface of the bioreactor.

In one embodiment, the culture is performed under anaerobic conditions. In another embodiment, the culture is performed under aerobic conditions. Extraction of the dopamine from the media may be done by any means, such as, but not limited to, filtration, precipitation, pressure, affinity bead extraction, ion chromatography, or resin purification.
Methods for Selecting or Identifying Probiotic Strains Capable of Producing Neurochemicals in the Gut and Enhancing Vaccination Response In one aspect, the present disclosure involves a method for selecting or identifying probiotic strains capable of producing neurochemicals in the gut of an animal or human. In one aspect, the method includes contacting a medium having a gastrointestinal-like environment with a probiotic strain for evaluation and detecting whether the probiotic strain produces neurochemicals in the medium.

In an aspect, the medium employed simulates gastrointestinal conditions of digestion. In an aspect, the medium employed provides a gastrointestinal-like environment to determine whether probiotic strains will physiologically function as neurochemical delivery vehicles to produce physiologically significant quantities of neurochemicals, such as dopamine in a gastrointestinal-like environment if given access to the dopamine precursor L-dopa.

The gastrointestinal-like environment possesses biochemical characteristics comparable to gastrointestinal contents. In an aspect, the medium includes precursor molecules for the evaluated probiotic strains to use in synthesizing neurochemicals, including for example L-dopa.

In an aspect, the medium includes a salivary phase, gastric phase, and intestinal phase. In an aspect, the medium comprises a simulated salivary fluid stock electrolyte and an amylase solution for the salivary phase. In an aspect, the medium comprises a simulated gastric fluid stock electrolyte and a pepsin solution for the gastric phase. In an aspect, the medium comprises a bile salt solution, a pancreatin enzyme solution, hemin, and a simulated intestinal fluid stock electrolyte for the intestinal phase.

In an aspect, the medium is an agar inoculated with the simulated small intestine medium comprising the salivary phase, gastric phase, and intestinal phase. In an aspect, the salivary phase and gastric phase a mixed together to produce gastric phase products. Thereafter, the gastric phase products are combined with the intestinal phase before cryopreservation and degassing.

In an aspect, the probiotic strain is a bacterial strain. In a preferred aspect, the bacterial strain is an *Enterococcus* spp. and/or *Vagococcus* spp. In an aspect, the methods include the detection of a production of neurochemicals on the medium. In an aspect, the production of neurochemicals on the medium is stimulated when combined with a precursor to the neurochemicals. In another aspect, the neurochemicals detected include dopamine, glutamate, serotonin, histamine, norepinephrine, epinephrine, phenethylamines, thyronamine compounds, tryptamine, GABA, acetylcholine and the like. In a preferred aspect, the neurochemicals detected include dopamine.

In an aspect, probiotic strains demonstrating neurochemical production in the amount of at least about 1 ng/g (nanogram/gram dry weight). In another aspect, probiotic strains demonstrating neurochemical production in the amount of at least about 1 µg/mL (micrograms/mL), at least about 5 µg/mL, at least about 10 µg/mL, at least about 20 µg/mL, at least about 30 µg/mL, at least about 40 µg/mL, at least about 50 µg/mL, at least about 60 µg/mL, at least about 70 µg/mL, at least about 80 µg/mL, at least about 90 µg/mL, at least about 100 µg/mL, at least about 110 µg/mL, at least about 120 µg/mL, at least about 130 µg/mL, at least about 140 µg/mL, at least about 150 µg/mL, or greater.

In another aspect, the methods can further include an initial step of screening a subject's microbiome for the presence or absence of bacterial strains capable of producing neurochemicals in the gut of the subject. Beneficially, it is identified herein that the microbiome can be a prolific source of dopamine in the gut, including the gastrointestinal track and provides a mechanism for efficacy of certain probiotic strains capable of producing the neurochemical dopamine.

In such an aspect, a biological sample is preferably received from a subject in a non-invasive manner and the biological sample is used to contact probiotic strains contained therein to the medium to determine the ability to produce neurochemicals in the gut of the subject. In variations, non-invasive manners of sample reception can use any one or more of: a permeable substrate (e.g., a swab configured to wipe a region of a subject's body, toilet paper, a sponge, etc.), a non-permeable substrate (e.g., a slide, tape, etc.), a container (e.g., vial, tube, bag, etc.) configured to receive a sample from a region of a subject's body, and any other suitable sample-reception element. In a specific example, samples can be collected from one or more of a subject's nose, skin, genitals, mouth, and gut in a non-invasive manner (e.g., using a swab and a vial). However, one or more biological samples of the set of biological samples can additionally or alternatively be received in a semi-invasive manner or an invasive manner. In variations, invasive manners of sample reception can use any one or more of: a needle, a syringe, a biopsy element, a lance, and any other suitable instrument for collection of a sample in a semi-invasive or invasive manner. In specific examples, samples can comprise blood samples, plasma/serum samples (e.g., to enable extraction of cell-free DNA), and tissue samples.

In such an aspect of the disclosure where bacterial strains are obtained from a sample of a subject, the growth and expansion of bacterial strains to be screened can be accomplished by standard methods known those of skill in the art. For example, probiotics and/or strains obtained from a subject are grown for a sufficient amount of time, for example, growth may be for 10, 11, 12, 13, 14, 15, 16, 17, 18, 19, or 20 hours. Likewise, incubation typically occurs at 37° C., however temperatures may be adjusted to influence, for example, growth rate of said strains.

In one embodiment, the methods of the present disclosure are useful to predict clinical benefits of treating a subject suffering from conditions such as, for example, gastrointestinal inflammation. In one aspect, the methods include screening the microbiome of the subject to determine the presence or absence of bacterial strains in the subjects' microbiome which possess the capability to produce neurochemicals, including dopamine, when combined with a neurochemical precursor, including L-dopa.

In another embodiment, the screening and targeting of the neurochemical production in the gut of a subject described according to embodiments of the invention provide targets for various therapeutic modalities. Such therapeutic modalities can include drug applications, synbiotic composition applications, and other therapeutic applications including general health and well-being of a subject.

Methods for Treating a Subject

In one aspect, the present disclosure involves a method for treating a vaccinated subject with a recent vaccination and/or need for gut health with a probiotic strain capable of producing neurochemicals in the gut of the subject. As one skilled in the art recognizes, there is a biochemical signaling in the gut-brain axis joining the microbiota, the alimentary tract (including the gastrointestinal tract) and the central nervous system. The gut-brain axis includes the microbiota in the alimentary tract, central nervous system, neuroendocrine and neuroimmune systems (e.g. hypothalamic-pituitary-adrenal axis), sympathetic and parasympathetic arms of the autonomic nervous system, and the gut microbiota.

The methods of treatment based on the ability to produce dopamine in the gut provide various other potential applications of use. One skilled in the art appreciates the production of dopamine is dependent on precursor substrate concentration, the target tissue and the differential expression of differing types of receptors/effector mechanisms. For example, in circular muscle, dopamine can induce contractions with an EC50 of $6.3 \times 10^{-6}$ mol/L. In contrast, in longitudinal muscle, dopamine can produce relaxation with an EC50 of $2.9 \times 10^{-5}$ mol/L. Disruption of the dopaminergic transporters results in altered colonic motility. The methods of treatment are thus further suitable for use in treating and/or preventing various gastrointestinal conditions, including for example, ulcers, namely gastric ulcers, diarrhea, inflammatory bowel disease (IBD) and associated symptoms and conditions, feeding conditions causing behavioral abnormalities, enterocolitis-type inflammation, and the like.

The methods of treatment are further suitable for use in treating and/or preventing various diseases and conditions associated with dopamine. In an exemplary aspect, inflammation, such as inflammatory bowel disease are well-suited for treatment and prevision as the provision of dopamine may alleviate and/or assist with treatment thereof. Accordingly, various other diseases and conditions associated with the neurochemical dopamine would benefit from the methods and/or compositions disclosed herein. Still further, the methods of treatment are further suitable for use in treatment and/or maintaining general health and well-being of a subject. In one aspect, the methods include administering to the subject a therapeutically effective amount of at least one probiotic strain and administering to the subject a therapeutically effective amount of a precursor and/or co-factor of the neurochemical in need of production in the gut of the subject. In an aspect, the subject is an animal or human.

One aspect of the present disclosure provides a method for enhancing immune response to a vaccine in a subject through the administration of a therapeutically effective amount of at least one dopamine producing probiotic to the subject. As will be demonstrated in the disclosure and examples that follow, it has been found that administration of a dopamine producing probiotic shortly before, concurrently with, and/or shortly following vaccination enhances the subject's immune response to the vaccine. In an embodiment, the dopamine producing probiotic is a bacterial strain, for example, *Enterococcus* spp. or *Vagococcus* spp. The dopamine producing probiotics of the present disclosure are capable of producing dopamine in the presence of L-dopa. In some embodiments, the bacterial strain is *Enterococcus faecium*. In an aspect, a therapeutically effective amount of the bacterial strain is from about $10^4$ CFU/g of probiotic to about $10^{14}$ CFU/g of probiotic, from about $10^4$ CFU/g of probiotic to about $10^{12}$ CFU/g of probiotic, from about $10^5$ CFU/g of probiotic to about $10^{11}$ CFU/g of probiotic, from about $10^5$ CFU/g of probiotic to about $10^{10}$ CFU/g of probiotic, from about $10^5$ CFU/g of probiotic to about $10^9$ CFU/g of probiotic, or from about $10^7$ CFU/g of probiotic to about $10^8$ CFU/g of probiotic, inclusive of every potential range therebetween, and wherein "CFU" is colony forming units.

In some embodiments, the dopamine producing probiotic is administered with a therapeutically effective amount of L-dopa. Notably, coverage of a wide range of L-dopa dosages is contemplated by the present disclosure. For example, the desired biological benefits of having *Enterococcus* convert L-dopa to dopamine as described herein may be achieved with a diet supplemented with L-dopa in ranges from about 0.1 mg L-dopa/kg animal feed to about 10 g L-dopa/kg animal feed. As used herein, "animal feed" is intended to mean the diet fed to an animal, including the diets of humans.

In some embodiments, to achieve a therapeutically effective amount of a dopamine producing product, lower or higher ranges of the *Enterococcus* and L-dopa may need to be given depending on the targeted application. Depending on a producer's aims and the animal species, supplementation at lower levels may yield an economically desirable cost-benefit ratio. In an aspect, a therapeutically effective amount of a precursor of dopamine, specifically L-dopa, can include from about 0.1 mg L-dopa/kg animal feed to about 10 g L-dopa/kg animal feed, from about 0.1 mg L-dopa/kg animal feed to about 5 g L-dopa/kg animal feed, from about 0.1 mg L-dopa/kg animal feed to about 1 g L-dopa/kg animal feed, from about 0.1 mg L-dopa/kg animal feed to about 500 mg L-dopa/kg animal feed, from about 0.1 mg L-dopa/kg animal feed to about 100 mg L-dopa/kg animal feed, from about 100 mg L-dopa/kg animal feed to about 1 g L-dopa/kg animal feed, from about 1 g L-dopa/kg animal feed to about 5 g L-dopa/kg animal feed, from about 5 g L-dopa/kg animal feed to about 10 g L-dopa/kg animal feed, or any range therebetween. Therapeutic ranges for other precursors and/or co-factors will depend on various factors present.

In another embodiment, probiotic strains produce dopamine in the gut of the subject in the amount of at least about 1 µg/mL (micrograms/mL), at least about 5 µg/mL, at least about 10 µg/mL, at least about 20 µg/mL, at least about 30 µg/mL, at least about 40 µg/mL, at least about 50 µg/mL, at least about 60 µg/mL, at least about 70 µg/mL, at least about 80 µg/mL, at least about 90 µg/mL, at least about 100 µg/mL, at least about 110 µg/mL, at least about 120 µg/mL, at least about 130 µg/mL, at least about 140 µg/mL, at least about 150 µg/mL, or greater. In further aspects, the probiotic strains produce dopamine in the gut of the subject in the amount of at least about 1 ng/mL to 1 mg/mL.

In an aspect, the probiotic strain is a bacterial strain. In a preferred aspect, the bacterial strain is an *Enterococcus* spp. and/or *Vagococcus* spp. Various *Enterococcus* spp., including *Enterococcus faecium* and *Enterococcus* hirae, are found in probiotic mixtures as well as in fermentation products. The bacteria are beneficially resistant to gastric juice and bile salts, a trait advantageous when attempting to deliver these organisms as an oral probiotic. Various *Vagococcus* spp. exhibit similar activity to the *Enterococcus* spp.

In an aspect, the precursor of the neurochemical is provided as a therapeutic agent. In a further aspect, the precursor of the neurochemical is provided as a food source. In a further aspect, the precursor of the neurochemical can be preloaded on the probiotic strain, such as a bacterial strain that is grown/germinated in a medium containing the precursor of the neurochemical.

In a preferred aspect, the precursor of the neurochemical is L-3,4-dihydroxyphenylalanine (L-dopa). In a further preferred aspect, the precursor L-dopa is provided from a food and/or dietary supplement source (e.g. herbal extracts), including for example plant foods including broad beans, *Mucuna pruriens, Vicia faba*, and sources from the genera *Phanera, Piliostigma, Cassia, Canavalia*, and *Dalbergia*.

Notably, *Mucuna pruriens* contains relatively high (3-7% dry weight) levels of L-dopa. In some embodiments, up to 88% of L-dopa can be extracted from *Mucuna pruriens* by boiling and soaking for approximately 48 hours. In other embodiments, efficiency of the process can be slightly improved by using approximately 0.25-0.50% sodium bicarbonate.

In an aspect, the precursor can be provided as the product of another bacterial strain, or as a co-culture with another strain, or as a pure chemical added, which generates the prebiotic composition. An exemplary precursor could be organisms containing tyrosine hydrolase which can convert tyrosine into L-dopa. In an aspect, the co-factor of the neurochemical dopamine can include pyridoxal phosphate (Pyridoxal 5-phosphate, PAL-P, PLP, Vitamin B6 phosphate).

In an aspect, the probiotic strain and precursor and/or co-factor of the neurochemical are co-administered in a single delivery system to the subject. In a further aspect, the single delivery system can be a co-formulation of the probiotic strain and the precursor and/or co-factor or a co-packaged formulation of the probiotic strain and the precursor and/or co-factor. In an alternative aspect, the probiotic strain and precursor and/or co-factor of the neurochemical are co-administered to the subject in distinct or separate delivery systems. In a further aspect, the probiotic strain and precursor and/or co-factor of the neurochemical can be separately administered in sequence, wherein the probiotic strain is administered first and thereafter the precursor and/or co-factor of the neurochemical is administered second. Alternatively, the probiotic strain and precursor and/or co-factor of the neurochemical can be separately administered in sequence, wherein the precursor and/or co-factor of the neurochemical is administered first and thereafter the probiotic strain is administered second.

In an aspect, the various embodiments of the probiotic strain and the precursor and/or co-factor of the neurochemical are administered orally to the subject. Oral administration can include various dosage forms as one skilled in the art will ascertain, including for example, tablets, capsules, aqueous or oily suspensions, solutions, emulsions, syrups or elixirs, dry products for reconstitution with water or other suitable vehicle before use. As described above, the present invention also provides an approach for optimization of synbiotic delivery of a probiotic or other dopamine producing product with a neurochemical precursor that the probiotic utilizes in the production of the desired neurochemical, in this case dopamine, so as to beneficially aid in the use of such products for the treatment of a variety of conditions and diseases, and particularly in the field of vaccines, whether prophylactic or therapeutic. The present disclosure relates to compositions effective for the production of dopamine at an industrial level. The compositions are low-cost and may be used to produce dopamine during fermentation. Methods and systems employing the compositions for the production of dopamine are also provided.

Methods for Producing Industrial Quantities of Dopamine

In one aspect, the present disclosure involves a method for producing dopamine for industrial applications. The methods include providing a natural or synthetic source of dopamine to beneficially aid in the use of such products for a variety of conditions and diseases. For example, the methods include synbiotic delivery of a probiotic with a neurochemical precursor to beneficially aid in the use of such products in the field of vaccines, whether prophylactic or therapeutic. In some aspects, a medium is utilized having a gastrointestinal-like environment, including either a precursor and/or co-factor for dopamine, or providing a precursor and/or co-factor to a medium in combination with the probiotic strain(s), and producing dopamine. In other aspects, any media can be employed and the probiotic strain is provided to the media in combination with either a precursor and/or co-factor for dopamine. Beneficially, the methods provide for the production of dopamine using any commercially-available media with the introduction of the precursor and/or co-factor for dopamine. In an aspect, the method for producing dopamine for industrial application further includes a step of isolating dopamine from the media.

In an aspect, any media suitable for inoculating a probiotic strain in combination with a dopamine precursor and/or co-factor as described herein can be employed for production of dopamine. Beneficially, it is the combined administration of the probiotic strain in combination with a dopamine precursor and/or co-factor on the media which provides increased conversion of the precursor and/or cofactor by the probiotic strain to produce dopamine as was not previously appreciated.

In an aspect, a medium employed simulates gastrointestinal conditions of digestion. In an aspect, the medium employed provides a gastrointestinal-like environment to determine whether probiotic strains will physiologically function as neurochemical delivery vehicles to produce physiologically significant quantities of neurochemicals, such as dopamine in a gastrointestinal-like environment if given access to the dopamine precursor L-dopa and/or a co-factor such as pyridoxal phosphate. In an aspect, the media possesses biochemical characteristics comparable to gastrointestinal contents. In an aspect, the media includes precursor molecules for the evaluated probiotic strains to use in synthesizing neurochemicals, including for example L-dopa and/or pyridoxal phosphate. In an aspect, the methods include producing dopamine grown on the media.

In an aspect, the media includes a salivary phase, gastric phase, and intestinal phase. In an aspect, the media comprises a simulated salivary fluid stock electrolyte and an amylase solution for the salivary phase. In an aspect, the media comprises a simulated gastric fluid stock electrolyte and a pepsin solution for the gastric phase. In an aspect, the media comprises a bile salt solution, a pancreatin enzyme solution, hemin, and a simulated intestinal fluid stock electrolyte for the intestinal phase.

In an aspect, the media is an agar inoculated with the simulated small intestine media comprising the salivary phase, gastric phase, and intestinal phase. In an aspect, the salivary phase and gastric phase a mixed together to produce gastric phase products. Thereafter, the gastric phase products are combined with the intestinal phase before cryopreservation and degassing. In an aspect, any methods of isolating dopamine from a medium employed herein can be employed as will be appreciated by those skilled in the art.

In an aspect, the probiotic strain is a bacterial strain. In a preferred aspect, the bacterial strain is an *Enterococcus* spp. and/or *Vagococcus* spp. as described herein. The precursors and/or co-factors described herein can be incorporated into a medium for the production of dopamine or alternatively provided to the medium with the probiotic strain for the production of dopamine. Beneficially, in an aspect of the invention, the bacterial strain conversion of the precursor and/or co-factor of dopamine into dopamine is at least about 10%, at least about 20%, at least about 30%, at least about 40%, at least about 50%, at least about 60%, at least about 70%, at least about 80%, at least about 90%, at least about 95%, or about 100% providing highly efficient production methods.

*Mucuna pruriens* Compositions

*Mucuna pruriens* compositions include a therapeutically effective amount of at least one *Mucuna pruriens* extract, bacteriostatic water, and a therapeutically effective amount of a co-factor of dopamine. As described above, *Mucuna pruriens* contains relatively high (3-7% dry weight) levels of L-dopa. In some embodiments, up to 88% of L-dopa can be extracted from *Mucuna pruriens* by boiling and soaking for approximately 48 hours. In other embodiments, efficiency of the process can be slightly improved by using approximately 0.25-0.50% sodium bicarbonate.

In some embodiments, a therapeutically effective amount of a *Mucuna pruriens* extract therefore can include from about 1 mg L-dopa/kg animal to about 10 mg L-dopa/kg animal at an optimal pH of about 3 to 8. In an aspect, a co-factor co-administered with *Mucuna pruriens* extract is pyridoxal phosphate. In another aspect, *M. pruriens* extract is provided as an infusion solution, injection solution, or a food supplement or in form of clysters.

Any *Mucuna pruriens* extract to be used for therapeutic administration can be sterile. Sterility is readily accomplished by filtration through sterile filtration membranes (e.g., 0.2 micron membranes). Therapeutic *Mucuna pruriens* compositions generally are placed into a container having a sterile access port, for example, an intravenous solution bag or vial having a stopper pierceable by a hypodermic injection needle.

*Mucuna pruriens* ordinarily will be stored in unit or multi-dose containers, for example, sealed ampoules or vials, as an aqueous solution or as a lyophilized formulation for reconstitution. The infusion solution is prepared by reconstituting the lyophilized *Mucuna pruriens* extract using bacteriostatic Water-for-Injection.

Another preferred embodiment of the disclosure relates to the use of extracts or extract-fractions or of extracted components, substances or mixtures of substances wherein the *Mucuna pruriens* components, substances, fractions or mixtures of substances are formulated as infusion solution, injection solution, for oral forms of application, as a therapeutic pack, a granulate, or a food supplement or in form of clysters. Yet another preferred embodiment of the disclosure relates to the use of extracts or extract-fractions or of extracted components, substances or mixtures of substances in oral, topical and/or parenteral applications.

The disclosure also provides a pharmaceutical pack or kit comprising one or more containers filled with *Mucuna pruriens* components, substances, fractions or mixtures of substances or the pharmaceutical compositions of the invention. Associated with such container(s) can be a notice in the form prescribed by a national health authority regulating the manufacture, use or sale of pharmaceuticals or biological products, which notice reflects approval by the agency of manufacture, use or sale for human administration. In addition, the *Mucuna pruriens* extracts of the present invention may be employed in conjunction with other therapeutic compounds.

In some embodiments, the cost of *Mucuna pruriens* varies from 0.55 USD/kg to 20 USD/kg. In other embodiments, L-dopa (kg) needed per metric ton of feed to achieve a therapeutically effective dosage can include from about 0.01 kg/per metric ton to 0.10 kg/per metric ton. In still other embodiments, the kilograms of *Mucuna* required per metric ton (10% *Mucuna*) can include from about 0.1 kg/per metric ton to 1 kg/per metric ton. In a preferred embodiment, the percentage of diet composed of *Mucuna* for animals under treatment ranges from 0.01% to 0.1%.

Regarding the low range estimate costs of *Mucuna pruriens* (i.e., to supply per metric ton of feed (USD)) ranges from 0.06 USD to 0.55 USD. For example, a mid-range estimate of costs of *Mucuna pruriens* extract may be 0.28 USD. High range estimate costs of *Mucuna pruriens* (i.e., to supply per metric ton of feed (USD)) ranges from 1.10 USD to 11.00 USD.

Notably, local prices for *Mucuna* can be quite inexpensive. However, internationally it is traded as a valuable supplement at greatly inflated value. Therefore, as a practice matter, dealing directly with producer/farmers is advisable if possible. In some embodiments, the reported yield for *Mucuna* is 1400 kg per acre. Farmers typically only make several hundred dollars per acre (~200 USD per acre of a similar legume like soybean).

Synbiotic Compositions

Synbiotic compositions include a therapeutically effective amount of a probiotic strain and a therapeutically effective amount of a precursor of a neurochemical. In some embodiments, a therapeutically effective amount of a probiotic strain can include from about $10^4$ CFU to about $10^{14}$ CFU. A therapeutically effective amount of a precursor of a neurochemical, specifically L-dopa, can include, for example, from about 0.1 mg L-dopa/kg animal feed to about 10 g L-dopa/kg animal feed.

In some embodiments, the probiotic strain of a bacteria of genus *Enterococcus* is utilized, achieving a therapeutic amount of *Enterococcus* with a diet supplemented with small amounts of L-dopa such as 100 mg L-dopa/kg animal feed, 10 mg L-dopa/kg animal feed or 1 mg L-dopa/kg animal feed. Depending on a producer's aims and the farm animal species, supplementation at these lower levels may yield an economically desirable cost-benefit ratio.

In an aspect, the probiotic strain is a bacterial strain. In a preferred aspect, the bacterial strain is an *Enterococcus* spp. and/or *Vagococcus* spp. In an aspect, the precursor of the neurochemical is L-3,4-dihydroxyphenylalanine (L-dopa). In an aspect, the co-factor is pyridoxal phosphate. In another aspect, the precursor L-dopa is provided from a food source and/or a therapeutic agent.

The synbiotic compositions are provided for oral administration. Oral administration can include various dosage forms as one skilled in the art will ascertain, including for example, tablets, capsules, aqueous or oily suspensions, solutions, emulsions, syrups or elixirs, dry products for reconstitution with water or other suitable vehicle before use.

Tablets and capsules for oral administration may be in unit dose form, and may contain conventional excipients such as binding agents, for example syrup, acacia, gelatin, sorbitol, or polyvinyl-pyrrolidone; fillers for example lactose, sugar, maize-starch, calcium phosphate, sorbitol or glycine; tableting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, polysorbate 80, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavoring or coloring agents.

Synbiotic compositions of the present disclosure are described in further detail in U.S. Pat. No. 11,357,803, which is herein incorporated in its entirety by reference.

All publications, patent applications, issued patents, and other documents referred to in this specification are indicative of the level of ordinary skill in the art to which this invention pertains and are herein incorporated by reference to the same extent as if each individual publication or patent application was specifically and individually indicated as incorporated by reference. Definitions that are contained in text incorporated by reference are excluded to the extent that they contradict definitions in this disclosure.

The present disclosure describes a "fit for purpose" use of a dopamine producing probiotic to accomplish a directed task; namely the modulation of dopamine-responsive immune elements that are involved in the generation of an immune response to a vaccine. In this regard, the herein described experiments have the potential to disclose a novel mechanism of action by which the host's immune response to a vaccination may be increased, thereby leading to greater protection from an infectious challenge. This approach of examining a mechanism of action by which a dopamine producing product may improve vaccination efficacy is uniquely different from prior studies which have examined the ability of probiotics to potentiate vaccination responses in the absence of any mechanisms of action.

The present disclosure is further illustrated by the following examples, which should not be considered as limiting in any way.

EXAMPLES

Example 1: Evaluation of *E. faecium* Production of Dopamine in the Presence of L-Dopa The present inventor contemplates an evaluation to demonstrate that in the presence of purified L-dopa, *E. faecium* isolated from healthy animals produce dopamine. The enzymatic synthesis of L-dopa to dopamine is shown in FIG. 1. Specifically, FIG. 1 shows the production of dopamine by *E. faecium* via decarboxylation of the precursor molecule L-dopa.

Figure 2A:
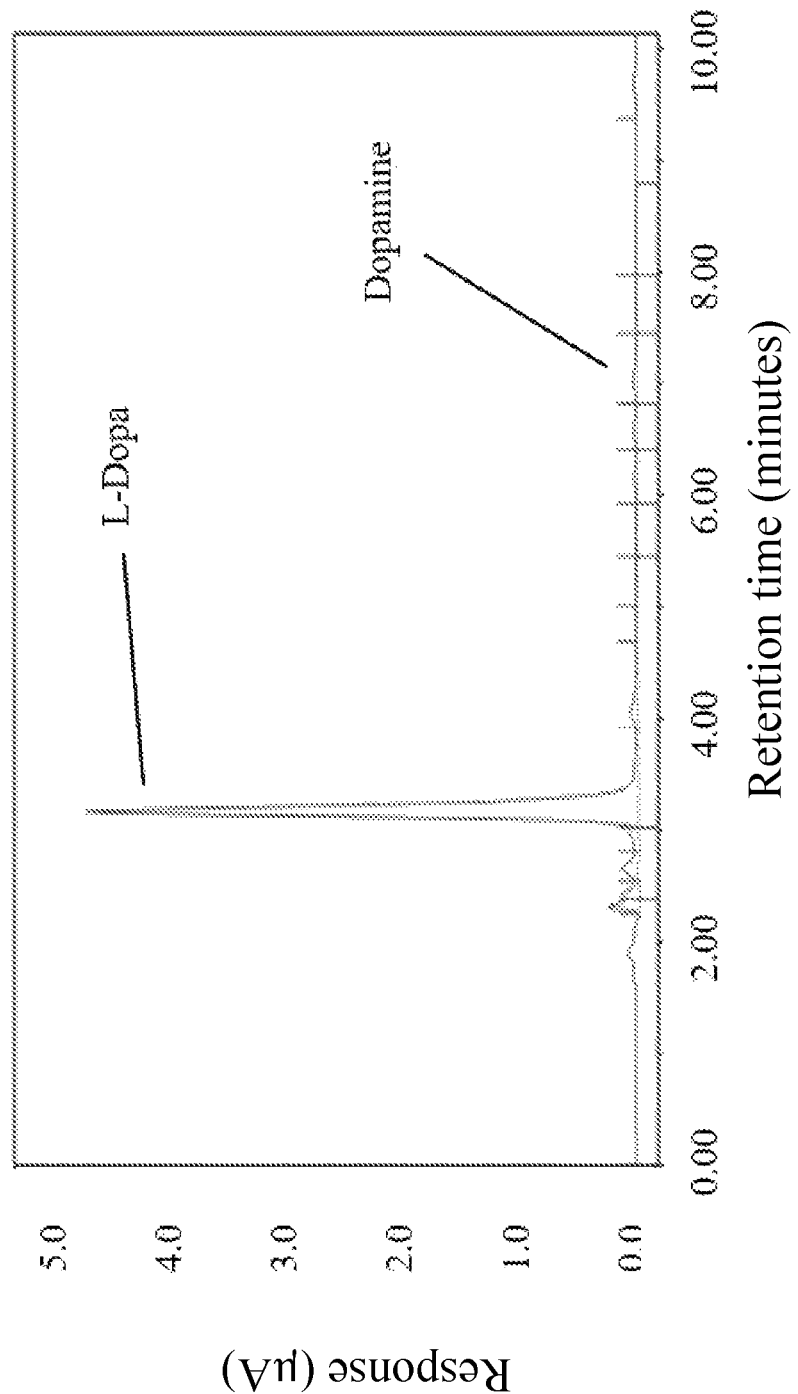
FIGS. 2A-2C show ultra-high-performance liquid chromatography with electrochemical detection (UHPLC-EC) chromatograms.
Figure 2B:
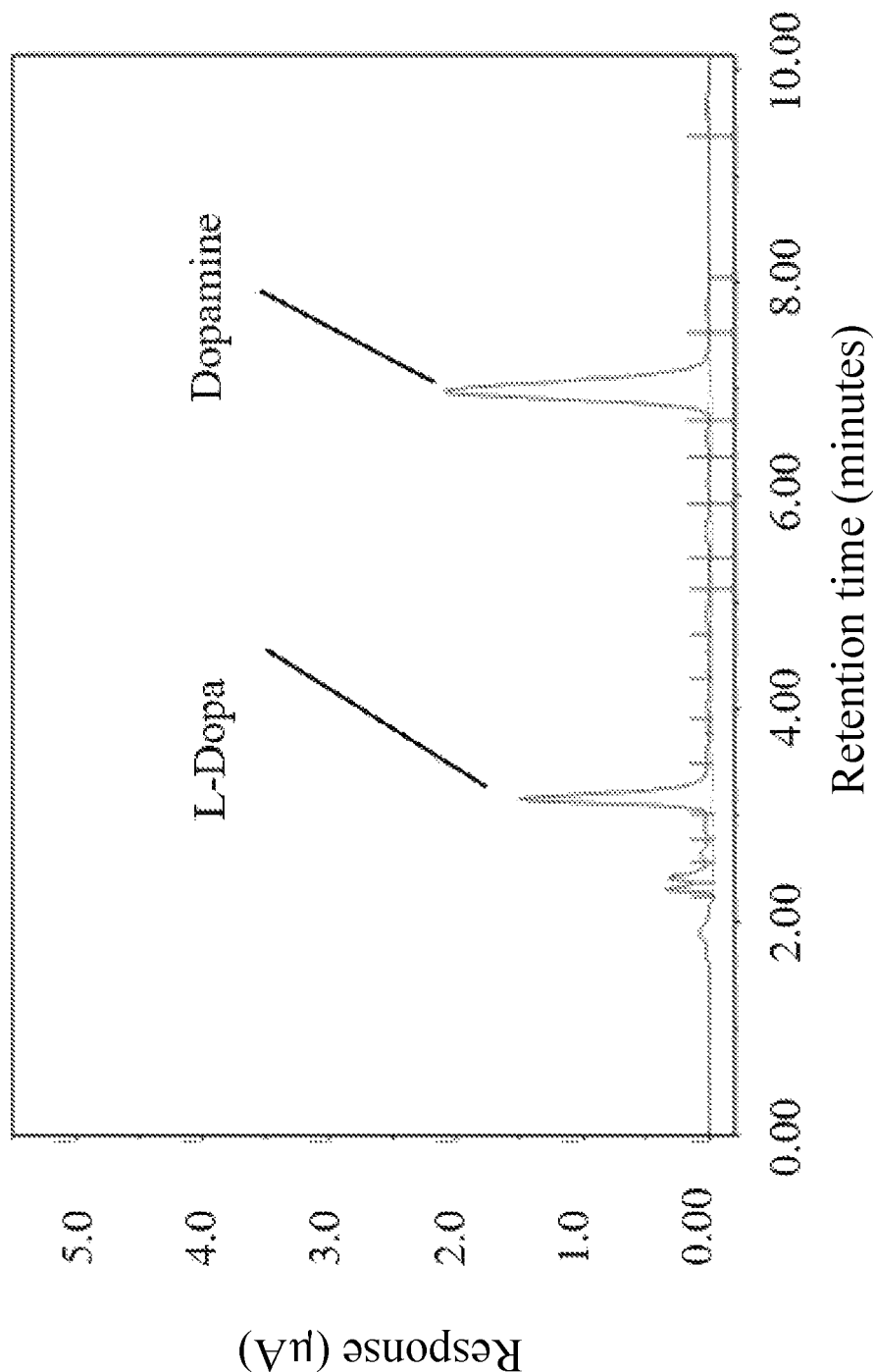
Figure 2C:
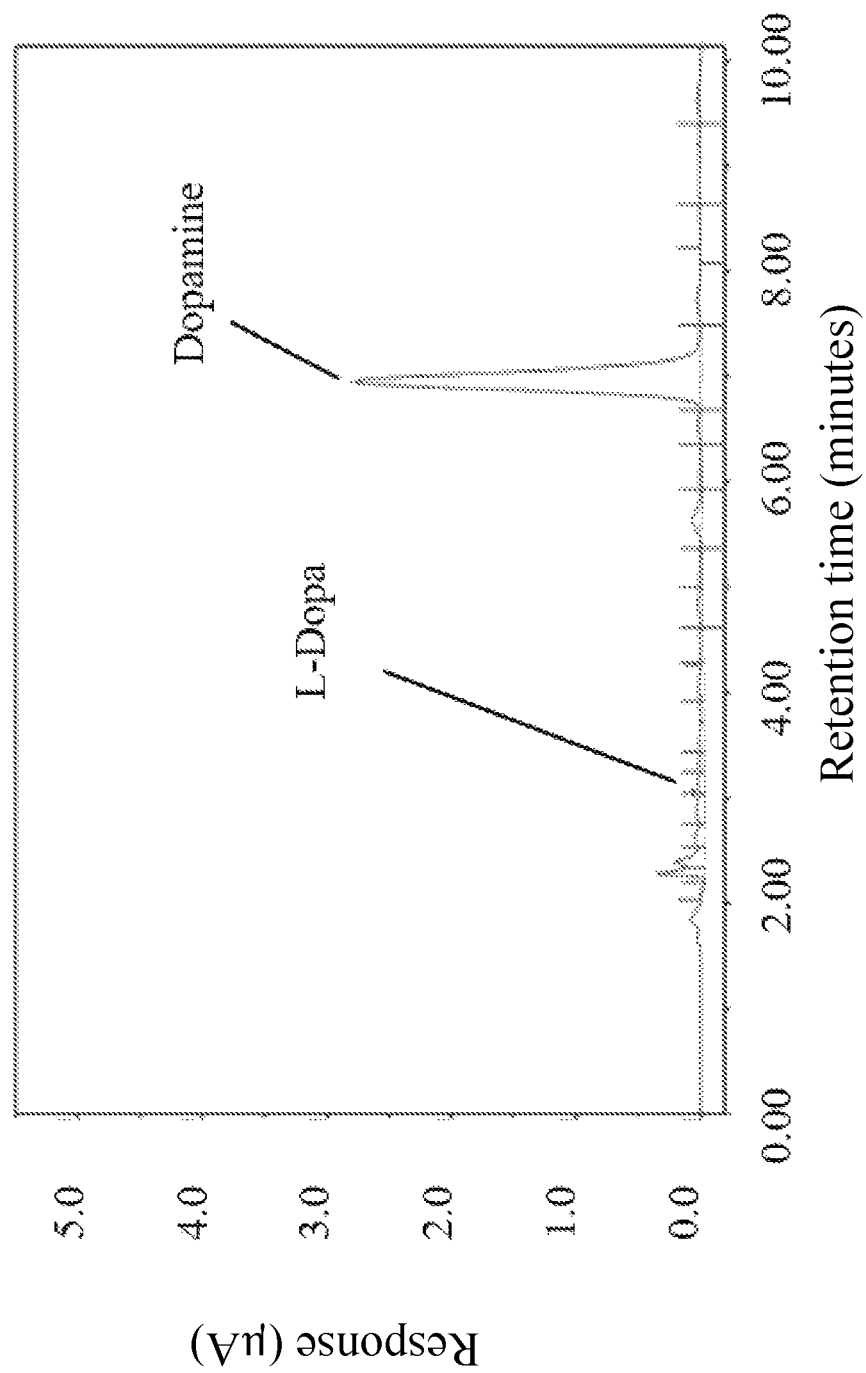

Further, FIGS. 2A-2C show UHPLC-EC chromatograms to further evaluate *E. faecium* production of dopamine in the presence of L-dopa. As shown in the FIG. 2A UHPLC-EC chromatogram), L-dopa added to growth medium in the absence of *E. faecium* only showed the presence of a L-dopa peak and no constitutive dopamine. FIG. 2B shows substantial but not complete enzymatic conversion of L-dopa to dopamine after overnight incubation in L-dopa containing medium with an *E. faecium* isolate according to embodiments of the invention. FIG. 2C shows complete conversion of all L-dopa to dopamine with another *E. faecium* isolate demonstrating the need to screen candidate *E. faecium* isolates for use according to embodiments of the invention.

Example 2: *E. faecium* Isolates Differ in the Capacity to Produce Dopamine

Figure 3:
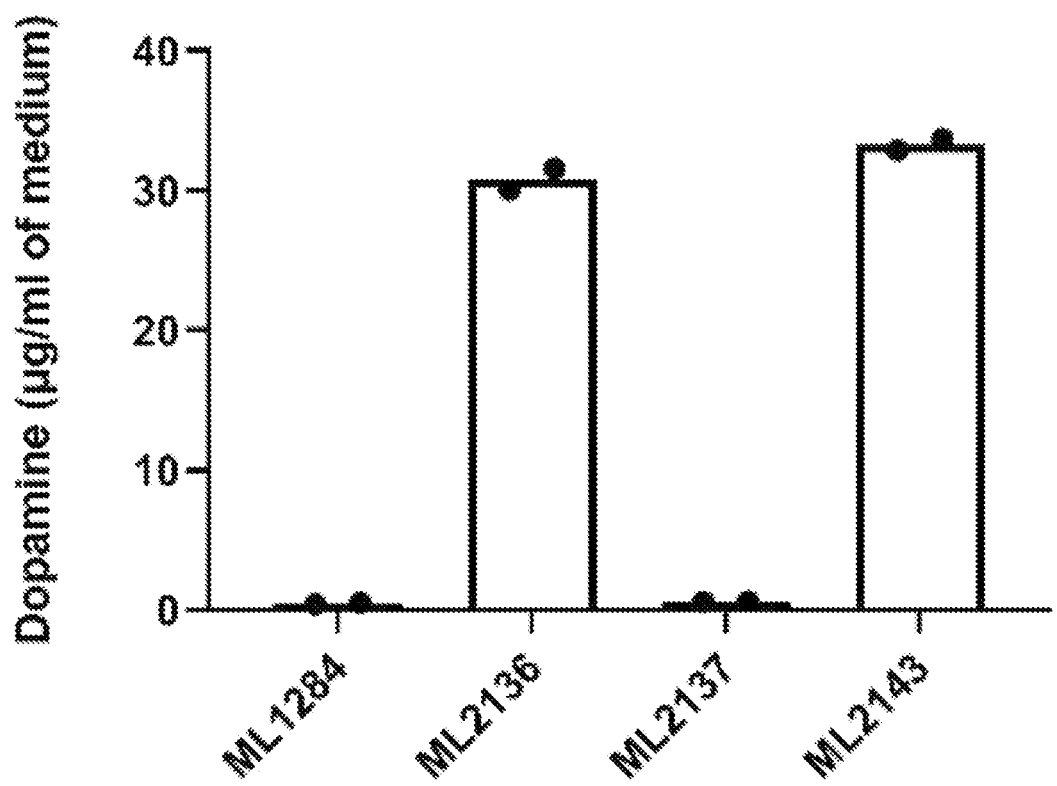
FIG. 3 shows that duplicate samples of E. faecium isolates ML2136 and ML2143 produce high levels of dopamine, while E. faecium isolates ML1284 and ML2137 do not when incubated for 24 hours in L-dopa supplemented with simulated intestinal medium according to embodiments of the invention. In other words, E. faecium isolates may differ in the capacity to produce dopamine.

Data obtained from broiler chickens demonstrate that *E. faecium* isolates from the intestine markedly differ in their ability to produce dopamine. As shown in FIG. 3, duplicate samples of *E. faecium* isolates ML2136 and ML2143 produced high levels of dopamine when incubated for 24 hours in L-dopa supplemented with simulated intestinal medium. However, *E. faecium* isolates ML1284 and ML2137 did not produce any detectable dopamine.

Example 3: *E. faecium* in the Presence of L-Dopa Produces Dopamine In Vivo

Figure 4:
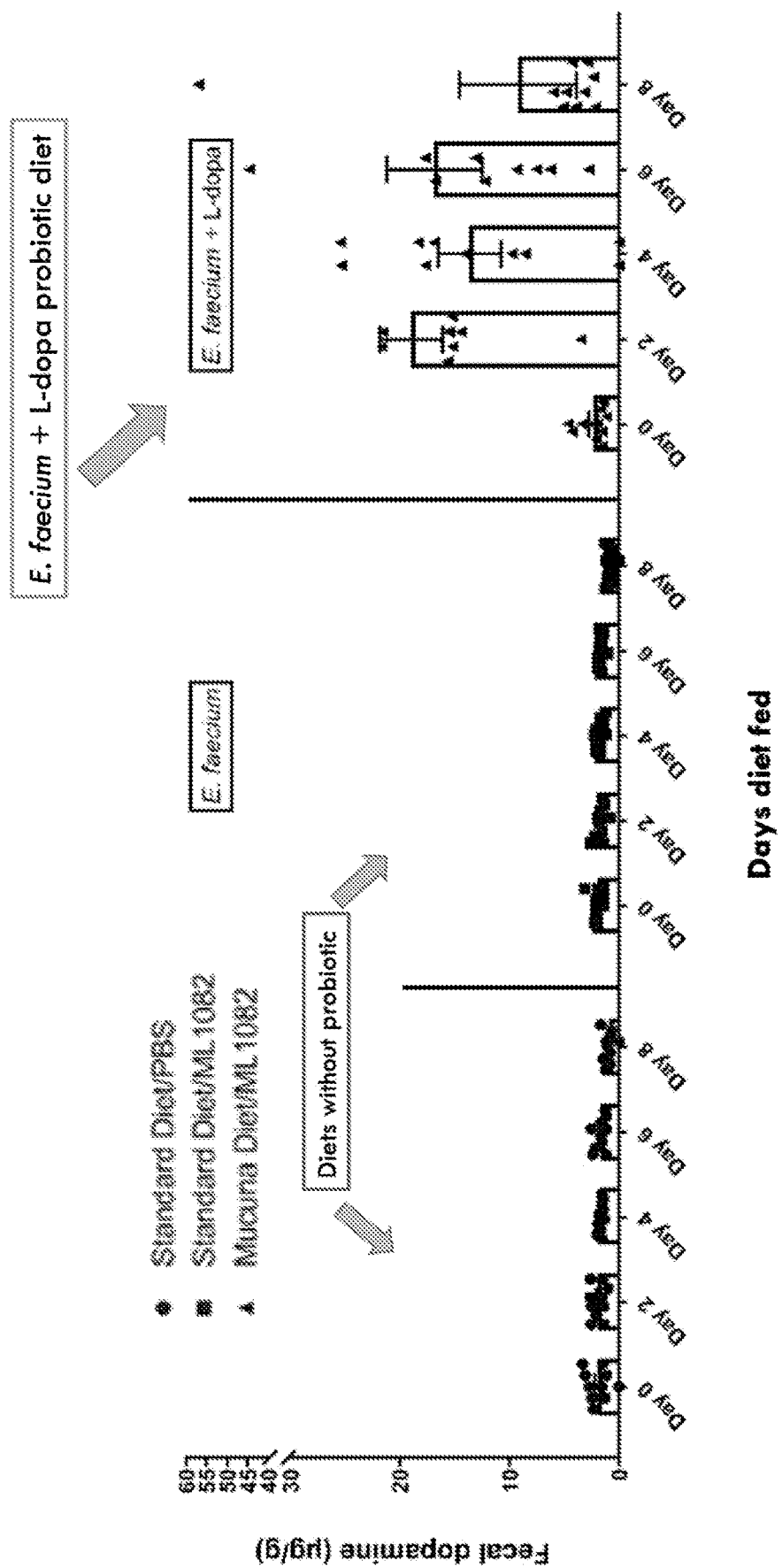
FIG. 4 shows that feeding of a diet supplemented with the probiotic E. faecium plus L-dopa is proven in vivo to result in increasing levels of dopamine within the gastrointestinal tract as evidence by with increased fecal levels of dopamine starting at Day 2 according to embodiments of the invention.

To demonstrate that feeding of the probiotic can achieve production of dopamine in vivo, an 8-day feeding trial utilizing 8-week old male CF-1 male mice was performed as shown in FIG. 4. Mice were divided into 3 groups of 10: Group 1, control; Group 2, *E. faecium* alone; and Group 3, *E. faecium*+L-dopa. For administration of *E. faecium*, mice were gavaged on a daily basis for one week with 0.2 ml of PBS containing $2 \times 10^8$ CFU of the probiotic. All animals which did not receive *E. faecium* received 0.2 ml of PBS. Groups were fed ad libitum with a granulated mouse chow that was, or was not, supplemented with L-dopa. During the 8-day trial period fecal pellets were collected at the start of the trial and at 2-day intervals thereafter and dopamine measured by ultra-high-performance liquid chromatography with electrochemical detection (UHPLC-EC). Feeding of the probiotic plus the L-dopa resulted in increased fecal levels of dopamine starting at Day 2 (FIG. 4).

Figure 5:
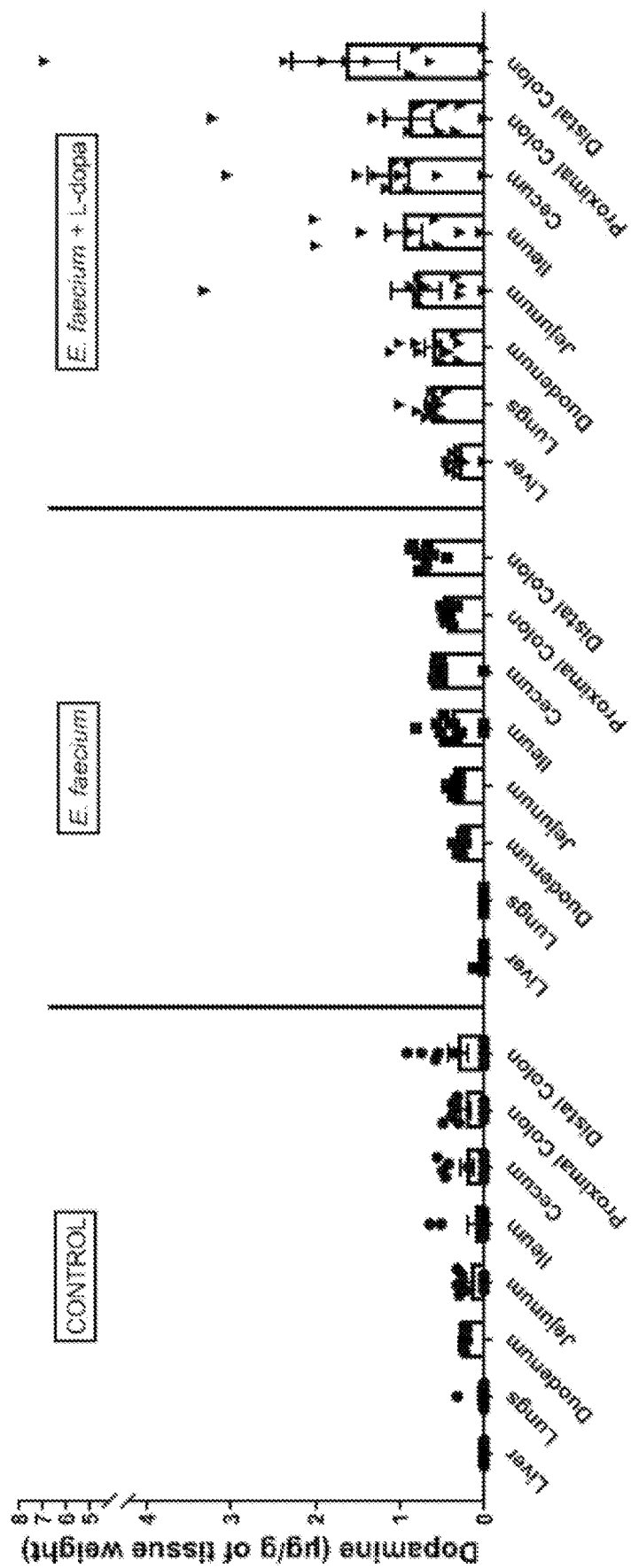
FIG. 5 shows that tissue levels of dopamine increase following the feeding of E. faecium plus L-dopa in the diet and that the increased levels of dopamine occurs in tissue specific regions where the development of immune responsiveness to vaccination is critical according to embodiments of the invention.
Figure 6A:
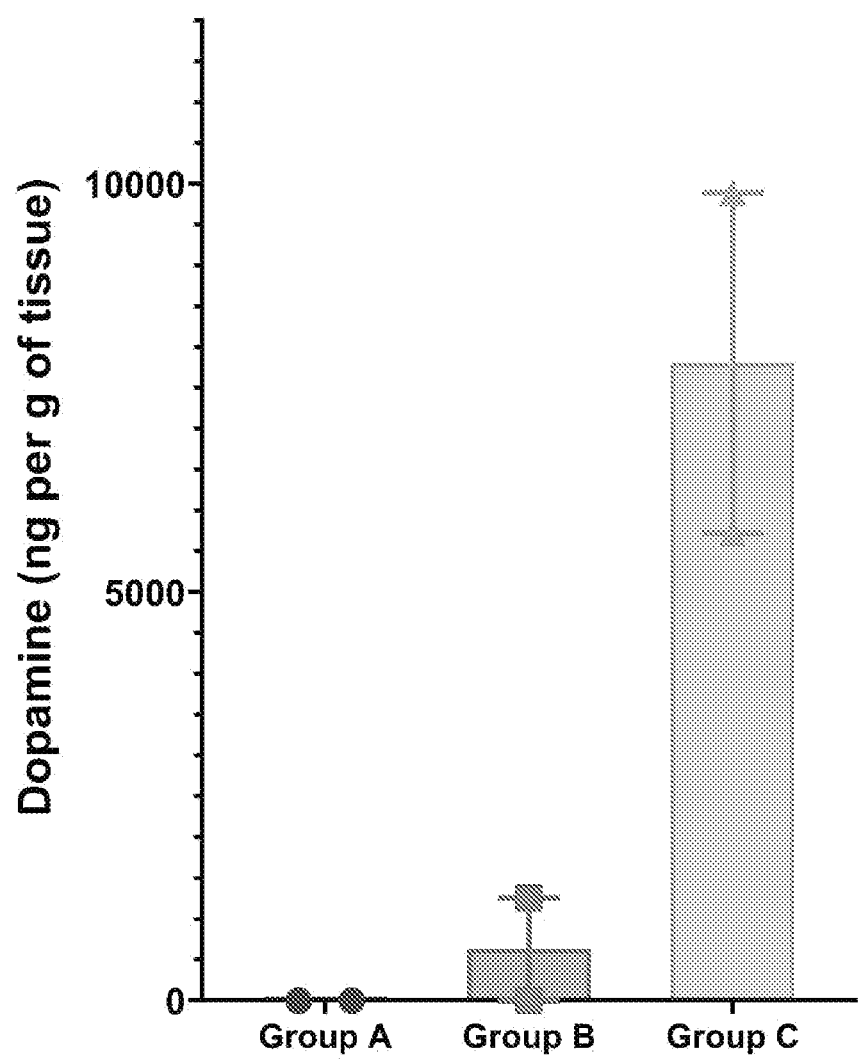
FIGS. 6A and 6B show that pigs fed a diet supplemented with L-dopa plus E. faecium diet experience a substantial increase in the concentration of dopamine present in either the duodenum tissue (6A) or contents (6B).
Figure 6B:
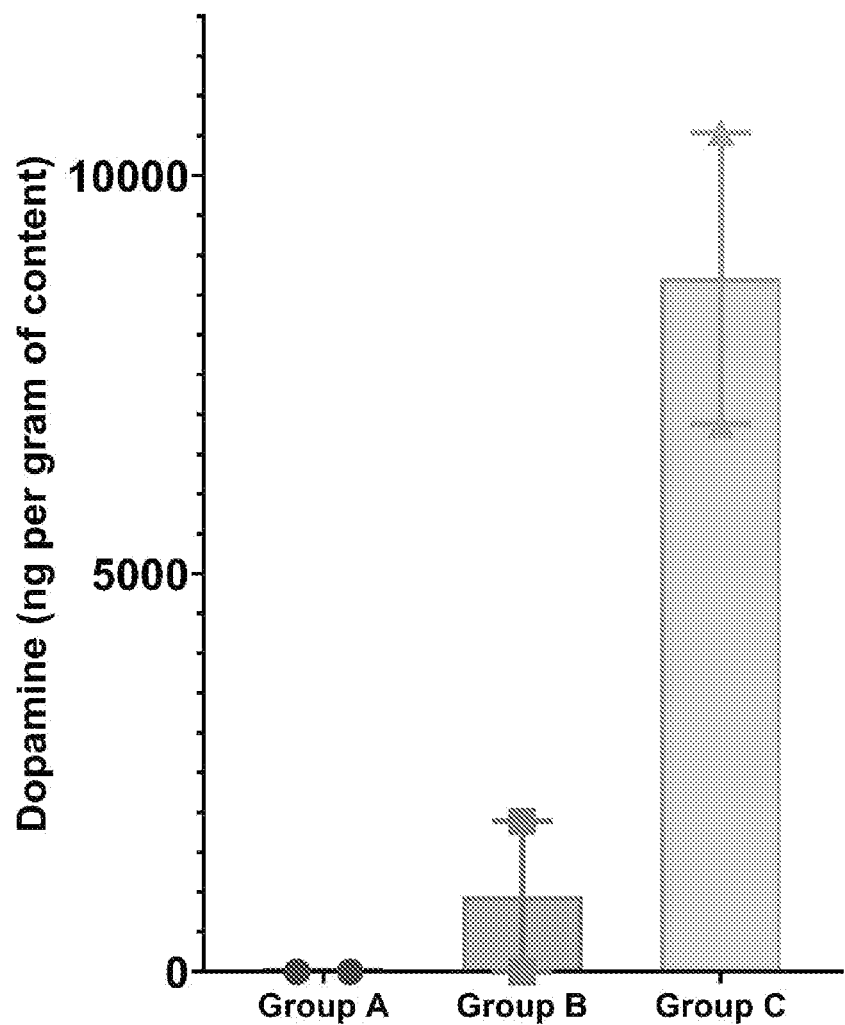

At the end of the 8-day feeding period animals were sacrificed and tissue dopamine was quantitatively determined using UHPLC-EC. As shown in FIG. 5, dopamine levels in the liver, lungs and all anatomical regions of the gut were increased in the group fed an *E. faecium* plus L-dopa supplemented diet as compared to other groups. This demonstrates that dopamine concentrations increased in tissue specific regions, importantly including the lungs, where the development of immune responsiveness to vaccination and subsequent challenge are most important.

Example 4: Time and Dose-Dependence of a Dopamine Producing *E. faecium* Probiotic The present inventor contemplates an evaluation of the dose-dependent ability of a dopamine producing *E. faecium* probiotic plus L-dopa precursor to influence neurochemical and immunological components in the gut and lung of healthy recently-weaned pigs. This approach may establish the dosage of the *E. faecium* probiotic needed to deliver dopamine in sufficient amounts to influence immunological components involved in the vaccination response. Specifically, the experiment may help determine the in vivo dose and time response kinetics of dopamine producing *E. faecium* probiotic on concentrations of dopamine within the intestinal tract. In some embodiments, L-dopa is not necessarily a requisite part of the diet if there is already enough L-dopa present in the diet.

Methods for establishing dose-dependence: The present inventor contemplates an evaluation wherein a dopamine producing *E. faecium* probiotic approved for feeding to pigs, may be determined to be negative for virulence-related factors. It is anticipated that such an in vitro test may convert up to 90% of L-dopa to dopamine. While *E. faecium* is present as a normal constituent of the gut microbiota, its level varies among individuals and as shown in FIG. 3. Not all *E. faecium* are capable of the conversion of L-dopa to dopamine. As such, a standardized amount of a known dopamine converter may be needed to achieve consistent levels of dopamine.

In a preferred embodiment, male pigs (3 weeks old) may be fed a commercial complete balanced ration with no antibiotics for 14 days with a diet supplemented with 0.2% of pure L-dopa or non-L-dopa-supplemented diet (Table 1). The inclusion of L-dopa may be needed to serve as substrate from which dopamine is synthesized (FIG. 1).

TABLE 1

Evaluation of in vivo dopamine production, time kinetics, and dosage range

| Groups [1] | Treatment[2] | Diet[3] |
|---|---|---|
| 1 | Control #1 | Normal pig feed |
| 2 | Control #2 | Feed plus 0.2% L-dopa |
| 3 | *E. faecium* 10E6 CFU | Feed plus 0.2% L-dopa |
| 4 | *E. faecium* 10E8 CFU | Feed plus 0.2% L-dopa |
| 5 | *E. faecium* 10E10 CFU | Feed plus 0.2% L-dopa |

[1] Group Size N = 5. Fecal and serum samples will be collected at 3 day intervals to monitor the consistency of dopamine elevation. At end of trial animals will be sacrificed and lung and intestinal tissue samples obtained for analyses
[2] CFU, colony forming units; dosage is per kg of feed
[3] Feed will be granulated and L-dopa at a final 0.2% w/w concentration.

Although L-dopa is normally found in animal feed, as well as foods in general due to its production by many plants, the use of a standardized amount in the feed is needed to ensure that enough L-dopa is present for the conversion to increase dopamine levels. In order to determine dose and time kinetics, in some embodiments fecal matter may be collected and concentrations of L-dopa, dopamine and the dopamine metabolites and breakdown products 3,4-dihydroxyphenylacetic acid (DOPAC) and homovanillic acid (HVA) may be determined by UHPLC-EC.

The present inventor contemplates that optimized feeding timepoints may be determined to be least 5 days prior to vaccination, at the time of vaccination itself, and continuing for at least 2 weeks after vaccination. In other embodiments, animals may be fed at least 7 days prior to vaccination, at the time of vaccination itself, and continuing for 2.5 weeks after vaccination. In yet another embodiment, animals are fed at least 10 days prior to vaccination, at the time of vaccination itself, and continuing for 3 weeks after vaccination. In another embodiment, animals may be fed at least 15 days prior to vaccination, at the time of vaccination itself, and continuing for 4 weeks after vaccination.

In some embodiments, the present disclosure describes a method for enhancing vaccine efficacy in a subject comprising administration of L-dopa probiotic strain(s) such as a bacteria of genus *Enterococcus* and/or administration of high L-dopa containing feeds. In a preferred embodiment, the therapeutically effective amount of L-dopa ranges from 1 mg/kg (907 mg/ton) to 10 mg/kg (9.07 g/ton). For example, the L-dopa needed for a 1 kg animal ranges from 1 mg to 10 mg. In another example, the therapeutically effective amount of L-dopa derived from *M. pruriens* ranges from 1 mg/kg, 5 mg/kg, or 10 mg/kg. Notably, in some embodiments, purified L-dopa alone may be used to enhance vaccine efficacy. In some embodiments, a purified L-dopa may be therapeutically effective when dosed at ranges from 0.1 mg/kg to 10 mg/kg. In other embodiments, a purified L-dopa may be therapeutically effective when dosed at ranges from 10 mg/kg to 1000 mg/kg.

Depending on the availability of L-dopa, a bacteria of genus *Enterococcus* can produce dopamine exceeding the needs of some animal hosts. As such, it is necessary to adjust the dosage of L-dopa to reflect considerations such as animal size, the bioavailability of L-dopa and the potency of dopamine for a given species. For this reason, as described above, coverage of a wide range of L-dopa dosages is contemplated by the present disclosure. For example, the desired biological benefits of having *Enterococcus* convert L-dopa to dopamine as described herein may be achieved with a diet supplemented with small amounts of L-dopa such as 0.01% (100 mg L-dopa/kg animal feed)(90.7 g L-dopa/ton animal feed), 0.001% (10 mg L-dopa/kg animal feed) (9.1 g L-dopa/ton animal feed) or 0.0001% (1 mg L-dopa/kg animal feed)(0.9 g L-dopa/ton animal feed). Depending on a producer's aims and the farm animal species, supplementation at these lower levels may yield an economically desirable cost-benefit ratio.

In other embodiments, dosage ranges may be adjusted according to the needs of the producer or physician to achieve the desired biological outcome. Testing in individual animal species (i.e., pig, chicken, human, cat, fish, etc.) are expected to indicate that higher dosages may be required to achieve efficacy in some instances. In these unique cases, diets containing a higher amount of L-dopa may be sought. For example, in some embodiments natural plant feed sources contain up to 10% L-dopa by weight (i.e., 100 g L-dopa/kg animal feed)(9.07 kg L-dopa/ton animal feed). In some embodiments therefore up to 10% L-dopa is utilized in a clinical setting. Dosing at this extreme is best fit for niche applications, such as in the keeping of exotic animals.

In other embodiments, dosage may be further refined based on alternative forms of L-dopa delivery which can enhance absorption and bioavailability. By means of non-limiting examples, L-dopa containing nanoparticles or enteric coating may be employed to achieve desirable L-dopa levels using less L-dopa than required by a traditional feeding blend. Additionally, further refinement of dosage may be accomplished by use of alternative forms of L-dopa delivery which can enhance absorption and bioavailability. By means of non-limiting examples, L-dopa containing nanoparticles or enteric coating may be employed to achieve desirable L-dopa levels using less L-dopa than required by a traditional feeding blend.

In some embodiments, trace amounts of dopamine can have potent effects. For example, infusion rates of 2-10 micrograms per kilogram (animal mass) per minute can facilitate increased cardiac output and enhanced vaccination response. In some embodiments, trace administration of dopamine is delivered intravenously from which it is very difficult to extrapolate what is needed by the per oral route. In other embodiments, a diet supplemented with 0.15% *Mucuna* (<0.0075% L-dopa diet/<75 mg L-dopa/kg feed) resulted in intestinal contents with a dopamine concentration 101 μM. Extrapolated to a chicken with 172 mL of small intestinal contents (small intestinal contents 162 g with density 0.94 g/mL; values from Takahashi, T., et al., Viscoelastic Properties of the Small Intestinal and Caecal Contents of the Chicken, *British Journal of Nutrition* 91(6), 867-872 (2004).

In some embodiments, delivery 17.1 micromoles of dopamine (2.6 milligrams of dopamine) to a chicken over the course of 3 hours is indicated. In another embodiment, at 14.44 micrograms/minute and a chicken mass of approximately 2 kg, a therapeutic effect is achieved. In another example, a mid-size 1 kg bird and a target of 2 micrograms/minute/kg body weight would require a diet near 10 mg L-dopa/kilogram feed. Notably, intestinal benefits like diarrhea control may be obtained with lower supplementation values as dopamine can act locally without the need to diffuse through the blood stream such as would be needed to influence cardiac output. Therefore, use of dosage ranges below this value may be justified. In some embodiments, even higher dosages beyond those disclosed above may be required as some animals will be less sensitive or have prolonged periods of gastrointestinal passage. In a preferred embodiment, optimization by species is required which often necessitates preparing for a broad range of possible dosages.

L-dopa sources and diet dose ranges for animal feed: In some embodiments, two sources of L-dopa may be used as the precursor to make dopamine by *Enterococcus*. One is the amount of *Mucuna pruriens* supplied L-dopa or chemically pure L-dopa that would be needed to supplement one tome of pig feed. Another natural source of L-dopa may be fava beans. While they do not contain as much L-dopa by percent weight as do *Mucuna pruriens* seeds, they may be even cheaper and are grown worldwide.

In another embodiment, dopamine is engineered into plants such as soybeans, tomatoes, and corn with techniques known in the art like homologous recombination, CRISPR, and the like. In yet another embodiment of the disclosure, a second, third, and/or fourth dopamine producing probiotic is used to create a multi-mixture. As the present disclosure is applicable to any vaccinated animal species, a wide range of animal feeds are contemplated by the disclosure, including chicken feed, cow feed, sheep feed, aquaculture feed, and the like. For instance, examples of chicken feed may include Chick Starter feed, Grower Feed, Layer Feed, Flock Raiser Feed, Broiler Feed, Game Bird Feed, Fermented Feed, and Cracked Corn.

Figure 7:
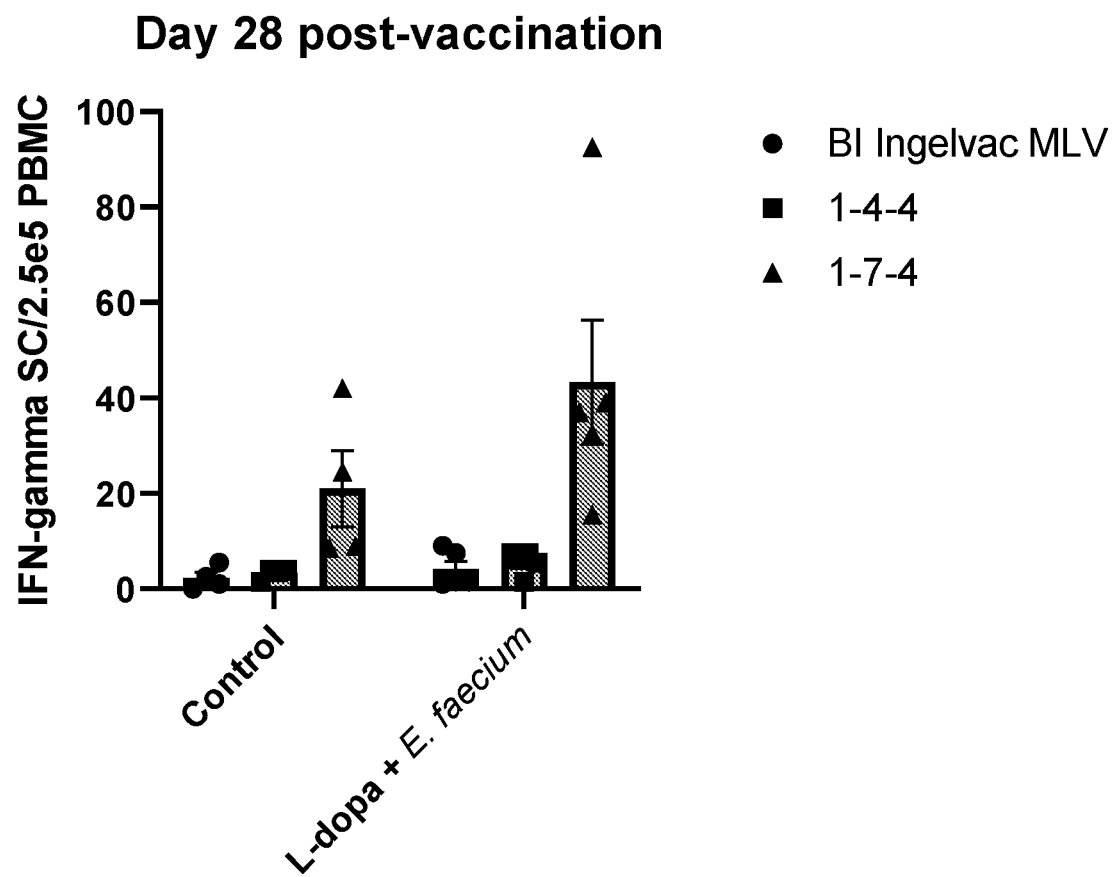
FIG. 7 shows that following vaccination for PRRSV, there are, on average, more PRRSV-specific interferon gamma producing cells in the peripheral blood of pigs that received a diet supplemented with L-dopa plus E. faecium than those that received the vaccination alone (Control). This demonstrates that the production of dopamine in the gut resulting from the feeding of L-dopa plus E. faecium can increase the production of interferon gamma by T cells following vaccination thereby increasing the protection of pigs to subsequent infection with live PRRSV.

As described above, very low-cost fermented dopamine may be made via transfection of a prokaryotic or eukaryote cell as described above. This scalable approach makes it feasible to generate low-cost dopamine at large scales and thereafter to encapsulate or otherwise package the fermented dopamine to give to animals in their feed. Encapsulation is a technology based on coating an active compound with one or more coating material and thereby providing improved stability and controlled section to target tissues. The present invention contemplates use of encapsulation such that the enclosed dopamine contents are released in a temporally and spatially controlled manner (i.e., the contents are only released in that region of the gut where it would be needed to achieve the desired biological effect.)

Example 5: Production of Dopamine in the Gut of Pigs Fed L-Dopa and *E. faecium*

Immediately upon receipt weaned 3 week old male pigs (2 pigs per group), were placed on either normal pig feed diet (Group A), L-dopa plus *E. faecium* supplemented (0.6 grams L-dopa+3×10E10 CFU *E. faecium* per kg of feed) diet (Group B), or L-dopa plus *E. faecium* supplemented (1.8 grams L-dopa+3×10E10 CFU *E. faecium* per kg of feed) diet (Group C). After 3 weeks of feeding animals were sacrificed and the concentration of dopamine in the gut was measured using UHPLC. As shown in FIGS. 6A and 6B, pigs fed the L-dopa plus *E. faecium* diet experienced a substantial increase in the concentration of dopamine present in both the duodenum tissue and contents. Furthermore, this increase showed dose dependency, with Group C having the highest concentration of dopamine present.

Example 6: Determining the Ability of the Dopamine Producing *E. faecium* to Influence the Immune Response to PRRSV Vaccination Methods: Immediately upon receipt weaned 3 week old male pigs (5 pigs per group), were placed on either normal pig feed diet (Control group) or L-dopa plus *E. faecium* supplemented (1.5 gram L-dopa+3×10E10 CFU *E. faecium* per kg of feed) diet (L-dopa+*E. faecium* group). One week later, at 4 weeks of age, all animals were vaccinated with 2 ml of the Boehringer-Ingelheim (BI) Ingelvac® modified live virus (MLV) vaccine intramuscularly in the neck. The BI Ingelvac® MLV vaccine is commonly used in the pig industry to protect against infection with PRRSV. At 28 days post vaccination, peripheral blood from the neck was obtained from the pigs and the number of immune cells producing the cytokine interferon gamma was assayed using the ELISpot technique.

Interferon gamma is an important cytokine in the adaptive immune response which has been shown to inhibit replication of PRRSV in vitro. Additionally, previous studies have shown that increased numbers of interferon gamma producing cells from peripheral blood in PRRSV challenged pigs correlates with lower levels of viremia. These findings suggest that the T cell response is likely more important than the antibody response for the partial immune protection conferred by PRRSV modified live virus vaccination. Thus, to evaluate the pigs, interferon gamma ELISpot assays were performed on peripheral blood mononuclear cells (PBMCs) from the control group and the L-dopa+*E. faecium* group.

The ELISpot assay is a combination of cell culture and ELISA that allows for the identification of specific white blood cells, primarily T cells, that recognize a pathogen and produce interferon gamma as a result. PBMCs were extracted from the blood and then plated at 250,000 live cells per cell on top of a polyvinylidene difluoride (PVDF)-backed microplate coated with anti-interferon gamma antibody. Three PRRS viruses (BI MLV and two wild type viruses, 1-4-4 and 1-7-4) were added to individual wells with cells from each pig. After washing away cells, virus, and unbound substances, a biotinylated polyclonal antibody that recognizes porcine interferon gamma was added to the wells. Following a wash, alkaline phosphatase conjugated to streptavidin was added to bind to the biotin. After removal of unbound enzyme, a substrate solution was added, resulting in blue-black precipitate spots where interferon gamma was secreted by individual cells. Interferon gamma producing cells (spots) can then be quantified using an automated ELISpot reader.

Results: At day 28 post-vaccination, there were, on average, more PRRSV-specific interferon gamma producing cells in the peripheral blood of pigs that received the dopamine producing probiotic than those without the probiotic (FIG. 7). It should be noted that values from one pig in the control group are not shown in FIG. 7 due to poor viability of the host cells. As shown in FIG. 7, the T cell interferon gamma producing response is most pronounced to the 1-7-4 wild type virus. The 1-4-4 and 1-7-4 nomenclature refers to the restriction fragment length polymorphism (RFLP) designation of different wild type PRRS viruses. While neither control or probiotic group shows a strong response to BI MLV, this is expected as the virus is adapted to MARC145 cells and grows slowly in porcine macrophages.

This data demonstrates that the production of dopamine in the gut resulting from the feeding of L-dopa plus *E. faecium* can increase the production of interferon gamma by T cells following vaccination thereby increasing the protection of pigs to subsequent infection with live PRRSV. These results also confirm the critical importance of dopamine in the generation of T cells following vaccination.

TABLE 2

Evaluating in vivo dopamine production on immunological response to PRRSV immunization

| Groups[1] | Treatment | Diet[2] | PRRSV Immunization[3] |
|---|---|---|---|
| 1 | Control | Normal pig feed | Yes |
| 2 | L-dopa + *E. faecium* | Feed plus L-dopa | Yes |

[1]Group size N = 5.
[2]1.5 grams L-dopa + 3 × 10E10 CFU *E. faecium* per kg of feed. Animals were fed ad libitum and weighed at end.
[3]PRRSV immunization occurred one week following start of feeding of probiotic. Animals were monitored for 28 days.

Figure 8:
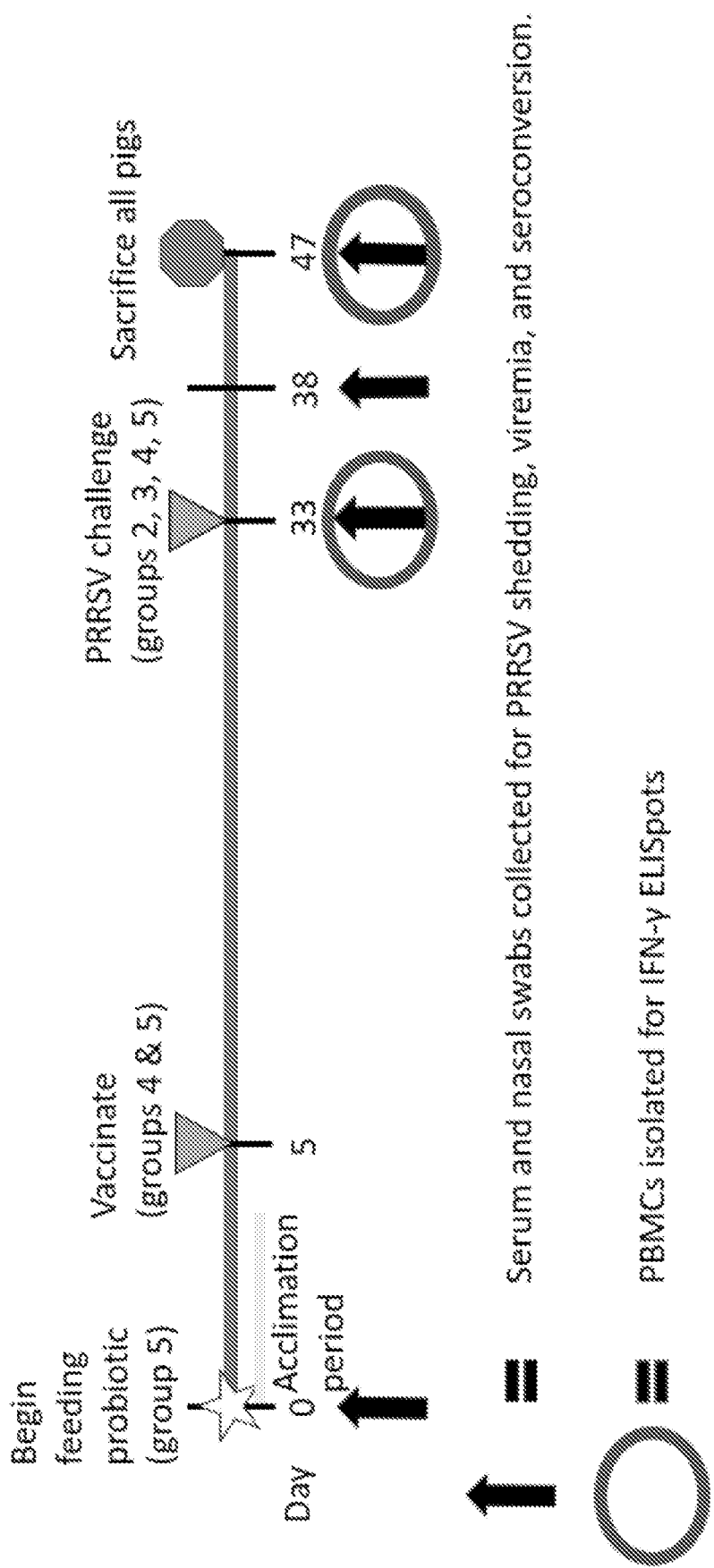
FIG. 8 depicts a schematic for a suggested experimental design to show that feeding of the E. faecium plus L-dopa diet results in enhanced PRRSV vaccine response according to embodiments of the invention.

Example 7: Evaluating the Ability of a Dopamine Producing *E. faecium* to Enhance the PRRSV Heterologous Immune Response Following MLV Vaccination in Weaned Pigs and Protect Against PRRSV Challenge Methods: Twenty-five 3-week-old pigs are anticipated to be obtained from a PRRSV-free herd, randomly divided into 5 rooms/groups with 5 pigs each (Table 3). Group 5 may be fed with *E. faecium* incorporated into the diet with additional supplementation of 0.2% L-dopa. Groups 2-5 may be vaccinated five days following the start of feeding of *E. faecium* probiotic to Group 5. At 28-days post-vaccination, groups 2-5 may be challenged with a contemporary PRRSV by intranasal injection. This contemporary strain of PRRSV may be the same one evaluated for serum neutralizing antibodies and IFN-gamma producing cells allowing for the evaluation of correlates of protection. All pigs are contemplated to be sacrificed at 14 days post-challenge (FIG. 8).

Serum will be drawn on days 0, 33, 38, and 47 and evaluated for viremia, seroconversion, and neutralizing antibodies. The same three viruses that are to be examined for neutralizing activity above will be tested again, allowing for homologous evaluation of the vaccine and challenge viruses and heterologous examination of the highly virulent variant virus. Nasal swabs are to be collected on days 0, 33, 38, and 47 and tested for shedding of PRRSV via PCR. Cell-mediated immunity will be assessed by interferon-gamma ELISpot from PBMCs collected on days 33 and 47. All pigs are to be scored daily for clinical signs of respiratory disease with temperatures taken at challenge and then every day after until sacrifice. Animals may be weighed upon arrival, at challenge, and at necropsy. Severity of gross and microscopic lesions are to be scored using a well-developed scoring system by a pathologist blinded to the treatment status of the pigs. Tissues (five sections of lungs, tracheobronchial lymph node) dare to be collected for assessment of severity of PRRSV-induced lung and lymphoid lesions. Immunohistochemistry is to be conducted to compare the amount of PRRSV antigen in the lungs and lymph nodes.

TABLE 3

To evaluate the effect of dopamine on the development of PRRSV immune protection

| Groups[1] | Treatment[2] | Diet[3] | PRRSV Immunization[4] | PRRSV Challenge[5] |
|---|---|---|---|---|
| 1 | Negative control | Normal pig feed | No | No |
| 2 | Positive control | Normal pig feed | No | Yes |
| 3 | No *E. faecium* | Feed plus 0.2% L-dopa | No | Yes |
| 4 | No *E. faecium* | Feed plus 0.2% L-dopa | Yes | Yes |
| 5 | *E. faecium* | Feed plus 0.2% L-dopa | Yes | Yes |

[1]Group size N = 5. Fecal and serum samples will be collected at 7 day intervals to monitor the consistency of dopamine elevation.
[2]CFU, colony forming units; dosage is per kg of feed. The CFU per kg of feed will be determined from performance of Table 1.
[3]L-dopa will be added to feed to achieve a final 0.2% W/W concentration. Animals will be fed ad libitum and will be weighed at end.
[4]PRRSV immunization will occur 5 days following start of feeding of probiotic. Animals will be monitored for 28 days.
[5]PRRSV challenge will occur 28 days after vaccination. All pigs will be sacrificed 14 days post challenge.

The present inventor anticipates that dopamine will achieve the predicted boost in post-vaccination PRRSV immunity. Notably, probiotic-treated and PRRSV-vaccinated group 4 may potentially exhibit an enhanced heterologous protection against challenge by a contemporary wild type PRRSV strain. This may be evidenced by a reduction in PRRSV-associated gross and microscopic lung lesions, viremia and nasal shedding.

Example 8: Industrial Production of Dopamine by Fermentation

The viability of industrial production of dopamine by fermentation is highly dependent on the affordability of substrates used in the growth medium. For this reason, an affordable minimalist composition may be developed. An initial formulation derived from a review of Zhang et. al (Zhang, G, Mills, D A, and Block D B, 2009, Development of Chemically Defined Media Supporting High-Cell-Density Growth of Lactococci, Enterococci, and Streptococci, *Applied and Environmental Microbiology,* 75:1080-87, herein incorporated in its entirety).

During dopamine production trials, L-dopa may be supplemented to 20 mM. In some embodiments, this medium fulfills the requirements for the robust growth of *E. faecium*, producing at least about $10^8$ CFU per mL of media. However, these conditions may be unsuitable for the production of dopamine and little to no dopamine production may be observed by strains of *E. faecium* grown in this media.

This potential lack of dopamine production, if observed, is likely due to the of *E. faecium* having a highly unique citric acid cycle and its deriving of energy from molecules typically ignored or secreted by other species of prokaryotes.

Many of these molecules are associated with fermentation and grain. Without being limited to a particular theory, it is believed that specialized carbohydrates or microbially derived cofactors may be necessary for the production of dopamine, the minimalist formulation described above may be further mixed with 15 g/L of Distiller's dried grains with solubles (also known as DDGs, Formulation E2). This variant proved successful both in supporting robust growth of *E. faecium* and in producing dopamine in excess of 2 g/L when L-dopa may be provided at 20 mM.

Dopamine may be extracted by first removing particulates through centrifugation and filtration. The filtrate may then be cooled and brought to a neutral pH to precipitate out the dopamine as the dopamine will form crystals at a neutral pH. Though this formulation may be successful, it would not be industrially useful to prepare a media in this manner. Purified amino acids and cofactors are prohibitively expensive.

Example 9: Demonstrating the Industrial Production of Dopamine Utilizing Various Media Augmented with the Neurotransmitter Precursor L-Dopa As shown in Table 4, significant levels of dopamine may be provided in commercially available laboratory media.

TABLE 4

Industrial production of dopamine using various *E. faecium* strains

|  | Media (Augmented by L-dopa prebiotic) | Average Dopamine Made (µg/mL) | Average Conversion Efficiency (%) |
|---|---|---|---|
| Strain ML1082 | TSB | 57 | 25% |
|  | LB | 44 | 20% |
|  | BHI | 54 | 24% |
|  | MRS | 13 | 6% |
| Strain ML1086 | TSB | 68 | 30% |
|  | LB | 43 | 19% |
|  | BHI | 69 | 30% |
|  | MRS | 55 | 24% |
| Strain ML1087 | TSB | 14 | 6% |
|  | LB | 16 | 7% |
|  | BHI | 8 | 3% |
|  | MRS | 7 | 3% |
| Strain ML1089 | TSB | 44 | 19% |
|  | LB | 20 | 9% |
|  | BHI | 48 | 21% |
|  | MRS | 28 | 12% |

As shown, several *E. faecium* strains were inoculated into broths supplemented with the prebiotic L-dopa at 0.0001M at approximately 5×10E6 CFU per ml of broth. Following 24 hours of static culture at 37° C. the amount of dopamine produced by the individual strains into the culture medium was assessed using UHPLC-EC. The media are as follows: TSB, tryptic soy broth; LB, Luria-Bertani broth; BHI, Brain-Heart Infusion broth; and MRS, deMan, Rogosa and Sharpe Lactobacilli broth.

Example 10: Evaluating the Ability of a Dopamine Producing *E. faecium* to Enhance the *Salmonella enteritidis* Immune Response Following Vaccination in Broiler Chickens

*Salmonella* contamination of chicken meat due to colonization within the chicken gut is a pressing food safety issue with USDA mandated zero tolerance for *Salmonella* in meat products. There is a recognized inability of *Salmonella* vaccination to adequately protect broiler chickens against *Salmonella* colonization in the gut. This is believed to be due to the short time (<8 weeks of life) in which the broilers are raised before being sacrificed and processed for use as a food/food ingredient. Accordingly, a trial was designed to test the ability of dopamine-producing *E. faecium* to improve *Salmonella* vaccine efficacy.

Methods: Forty-eight, Cornish rock, one-day old chicks of both sexes, were obtained and housed in groups of 12 animals per pen with free access to food and water. Animals were divided into four groups according to Table 5.

TABLE 5

| Groups | Treatment | Diet | Salmonella Immunization | Salmonella Challenge |
|---|---|---|---|---|
| 1 | Control | Normal chicken feed | No | Yes |
| 2 | Vaccinated Control | Normal chicken feed | Yes | Yes |
| 3 | Pre- and probiotic dose #1 | Normal chicken feed plus dose #1 | Yes | Yes |
| 4 | Pre- and probiotic dose #2 | Normal chicken feed plus dose #2 | Yes | Yes |

Chickens were fed either a normal chicken feed or feed plus a pre- and probiotic L-dopa composition based on the treatment group. The pre- and probiotic compositions were formulated as follows:

Dose #1 (Group 3): For each kilogram of feed, 2.5 grams of L-dopa containing finely ground *Mucuna* powder and 0.3 grams of dried *Enterococcus faecium* (5×10E10 CFU per gram) were added and well mixed. The *Mucuna* provided 0.175 grams of L-dopa per kilogram of feed.

Dose #2 (Group 4): For each kilogram of feed, 10.0 grams of L-dopa containing finely ground *Mucuna* powder and 0.3 grams of dried *Enterococcus faecium* (5×10E10 CFU per gram) were added and well mixed. The *Mucuna* provided 0.700 grams of L-dopa per kilogram of feed.

On day 7 of age, Groups 2, 3, and 4 were vaccinated with a live culture *Salmonella typhimurium* vaccine. On day 26 of age, all four groups were challenged with 5×10E6 CFU of live nalidixic acid and novobiocin resistant *Salmonella enteritidis* per animal. Half of each group was sacrificed on day 34 of age and the remaining animals were sacrificed on day 35. At time of sacrifice, cecal tissue and cecal contents were removed and weighed.

Data Analysis: Measurements of dopamine and dopamine metabolites in tissue and contents were performed by Ultra-High Performance Liquid Chromatography with Electro-chemical (UHPLC-EC) detection based on methodology known in the art (Frattini V, Lionetti C. Histamine and histidine determination in tuna fish samples using high-performance liquid chromatography. Derivatization with omicron-phthalaldehyde and fluorescence detection or UV detection of "free" species. J Chromatogr A. 1998; 809(1-2):241-5; doi: 10.1016/s0021-9673(98)00157-5; Cicero A, Galluzzo F G, Cammilleri G, Pulvirenti A, Giangrosso G, Macaluso A, et al. Development of a Rapid and Eco-Friendly UHPLC Analytical Method for the Detection of Histamine in Fish Products. Int J Environ Res Public Health. 2020; 17(20); doi: 10.3390/ijerph17207453; and Vitali L, Valese A C, Azevedo M S, Gonzaga L V, Costa A C, Piovezan M, et al. Development of a fast and selective separation method to determine histamine in tuna fish samples using capillary zone electrophoresis. Talanta. 2013;

106:181-5; doi: 10.1016/j.talanta.2012.12.020, each herein incorporated by reference for this purpose).

To quantify *S. enteritidis* colonization of cecal contents, cecal contents were homogenized in 5 ml of saline using a vortex set at maximal speed. A standard serial dilution series of Petri dish plates were set up according to accepted standard microbiological procedure using the BD Difco™ Dehydrated Culture Media Xylose Lysine Deoxycholate (XLD) agar (BD, catalog #DF0788-17-9) supplemented with antibiotics (20 µg/mL nalidixic acid and 25 µg/mL novobiocin; Sigma Chemical Co., St. Louis, MO). Following overnight incubation at 37° C. in a standard incubator, plates were removed, and number of colonies were counted.

Figure 9A:
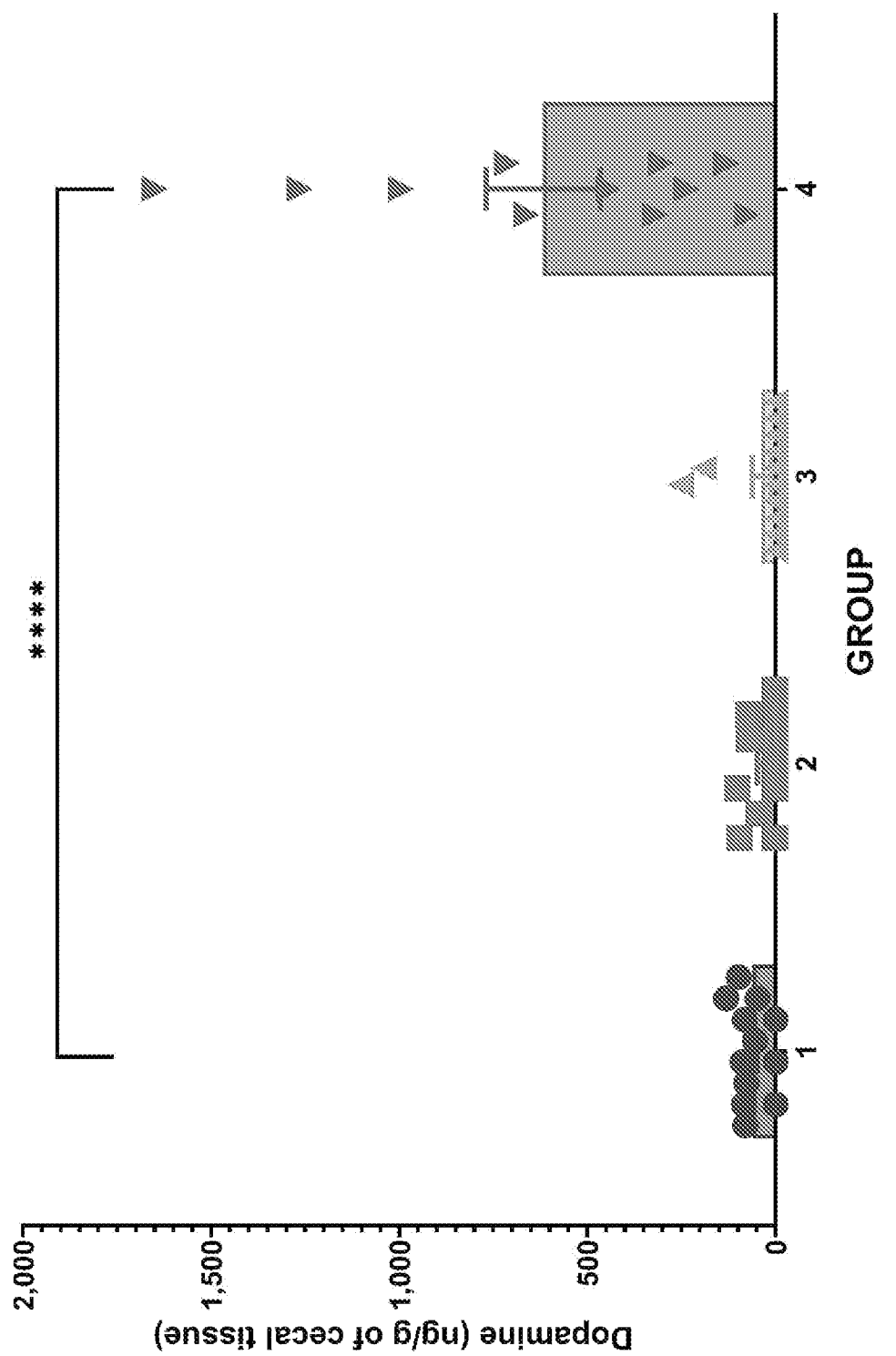
FIGS. 9A-9E shows that feeding a diet supplemented with the probiotic E. faecium plus L-dopa increases production of dopamine in the gut and increase the ability to retard colonization by Salmonella enteritidis.
Figure 9B:
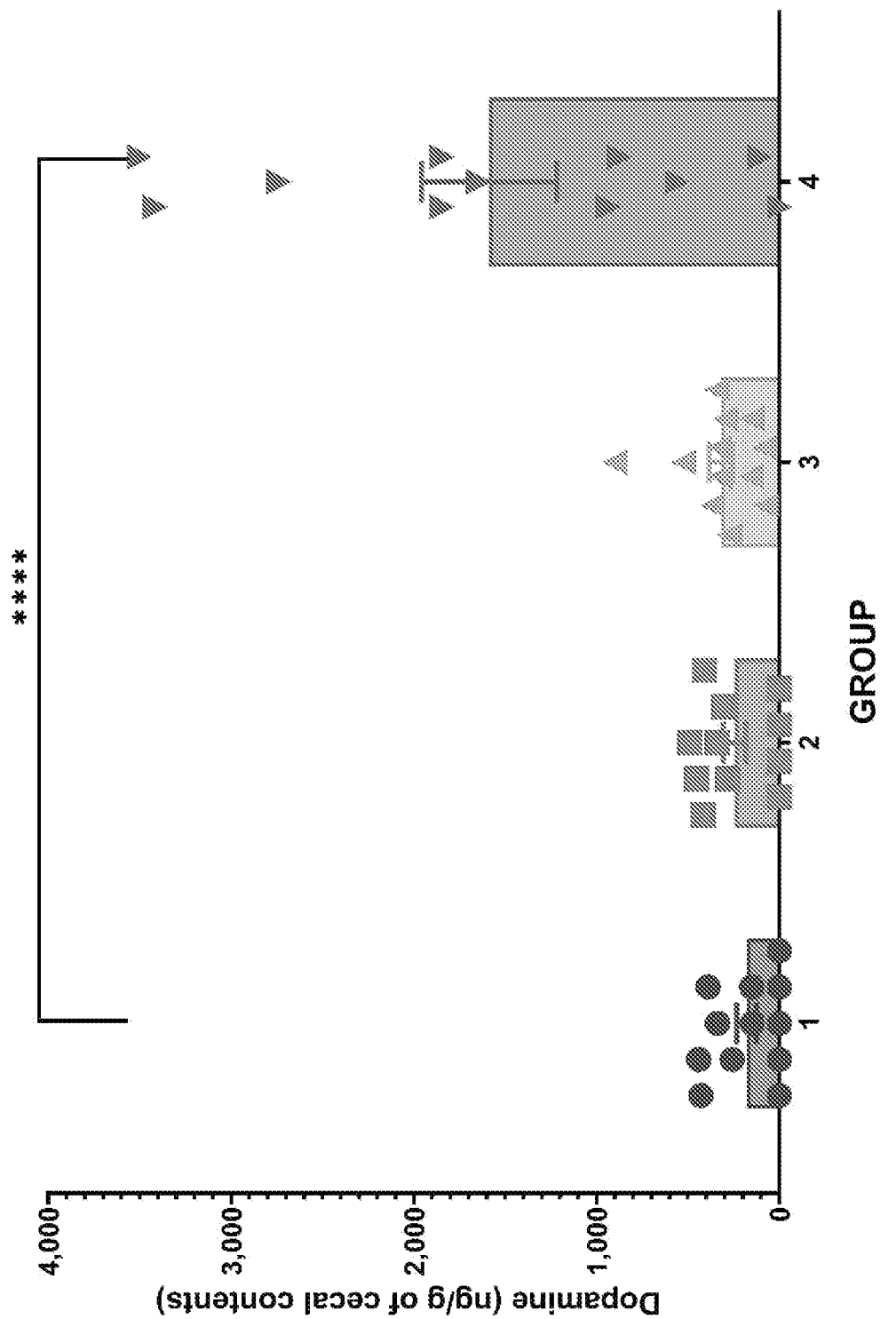
Figure 9C:
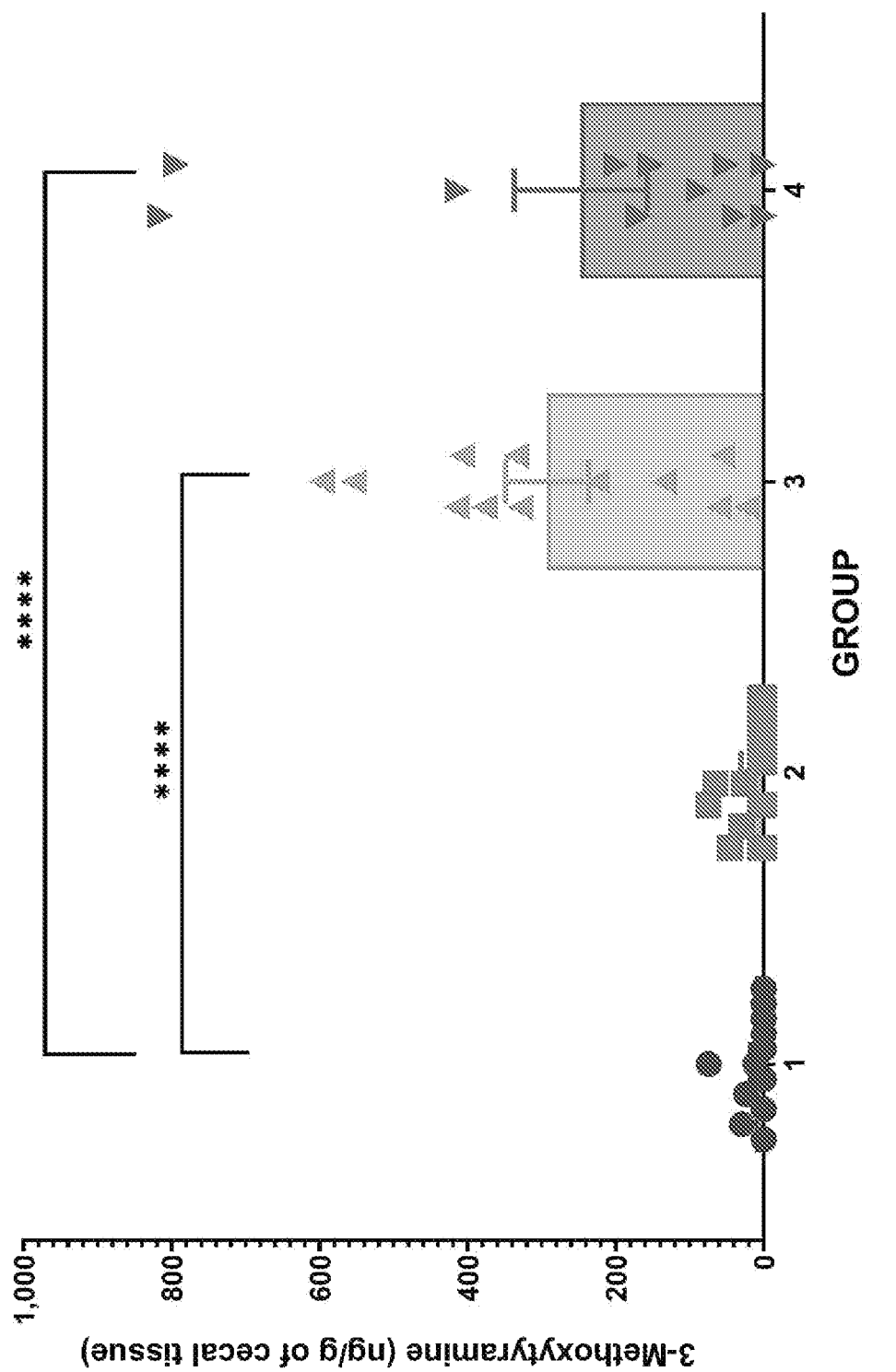
Figure 9D:
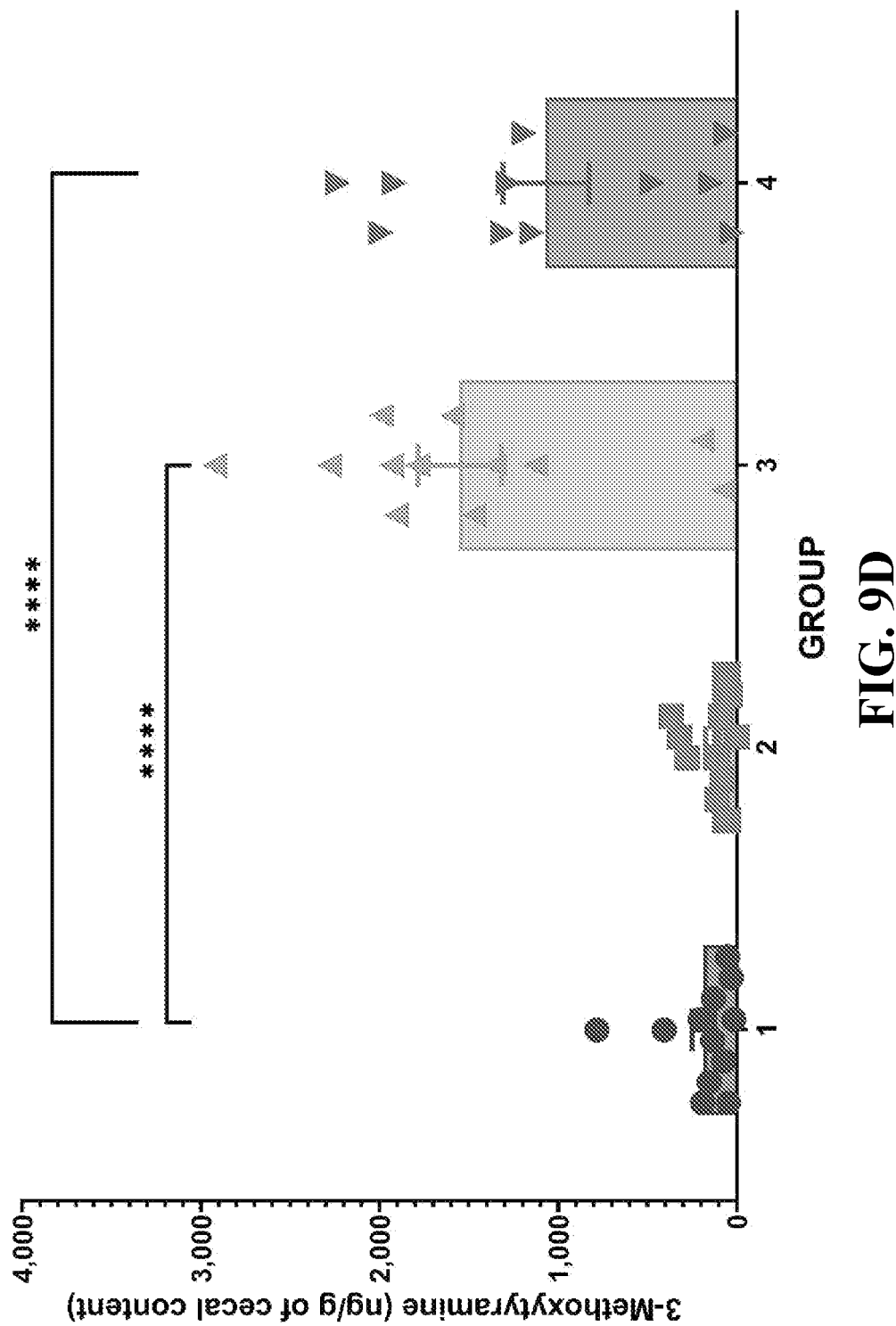

Results: As shown in FIGS. 9A-9E, the use of the dopamine-producing probiotic *E. faecium* resulted in a high production of dopamine in the gut (FIGS. 9A-9D). Group 4 had significantly increased levels of dopamine in the cecal tissue (FIG. 9A) and cecal contents (FIG. 9B). This was not seen in Group 3, which was fed a smaller concentration of the L-dopa containing *Mucuna* prebiotic. However, as shown in FIGS. 9C and 9D, both Group 3 and Group 4 had significantly increased levels of the dopamine metabolite 3-methoxytyramine in the cecal tissue (FIG. 9C) and cecal contents (FIG. 9D) as compared to Groups 1 and 2. This is an important finding as it shows that the production of dopamine in the gut for Group 3 does in fact result in a demonstrable level of dopamine as there would not be any presence of dopamine's metabolite 3-methoxydopamine without dopamine being present in the first place. This further demonstrates that for Group 4, very high levels of dopamine production in the gut are occurring from the action of the probiotic. Unlike Group 3, the level of dopamine production in Group 4 exceeds the host's degrative pathways to completely process dopamine on an ongoing basis into its constitutive metabolite. This is why Group 4 has higher levels of dopamine but lower levels of 3-methoxydopamine as compared to Group 3.

Figure 9E:
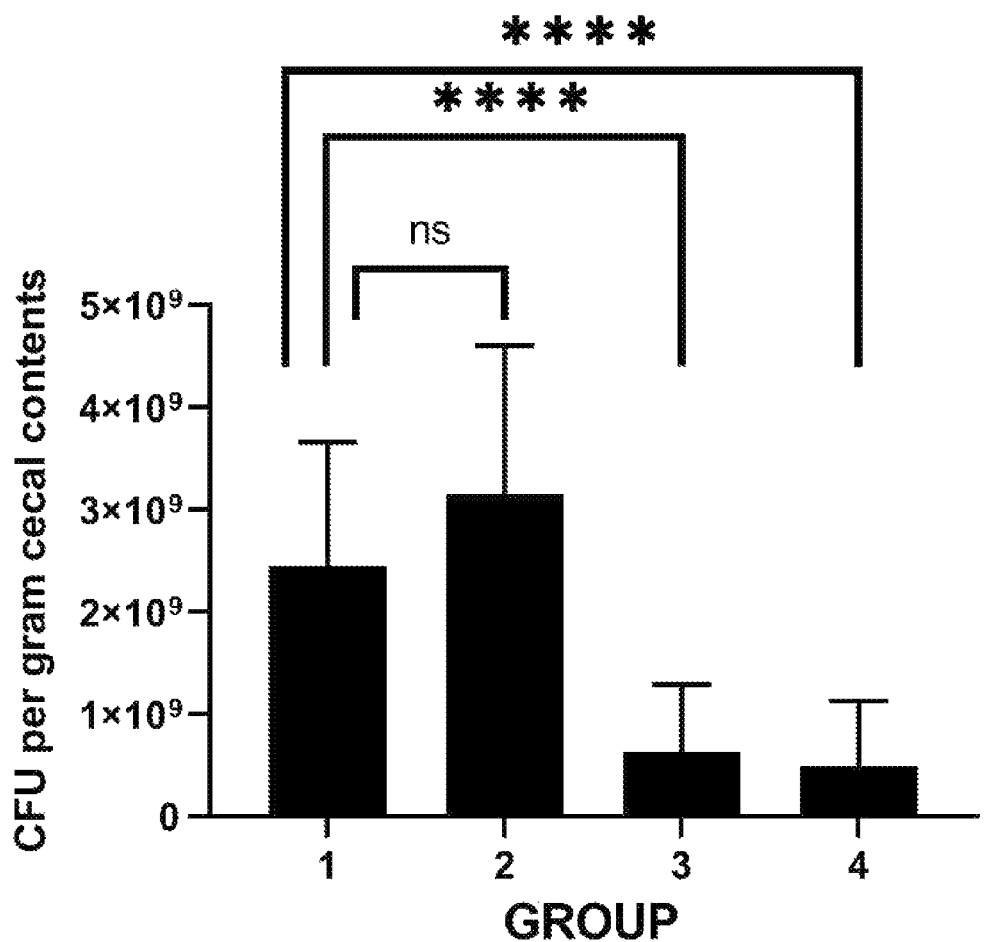

Additionally, the two groups that received the dopamine-producing probiotic *E. faecium* diet, Groups 3 and 4, demonstrated increased ability to retard colonization of the cecum by *S. enteritidis* (FIG. 9E). Thus, these results demonstrate that the use of a dopamine-producing probiotic can increase the efficacy of an oral vaccine, thereby protecting the host from subsequent infection and tissue colonization. Although this is shown for an oral vaccine, those having ordinary skill in the art would immediately realize the concept can be applied to other routes of vaccination, i.e. nasal, I.M. or other routes.

What is claimed is:

1. A method for enhancing immune response to a vaccine in a subject, the method comprising:
    administering a therapeutically effective amount of at least one dopamine producing probiotic to the subject, wherein the at least one dopamine producing probiotic comprises *Enterococcus faecium* and wherein the probiotic is administered with a therapeutically effective amount of L-dopa, and
    administering a vaccine for porcine reproductive respiratory syndrome virus (PRRSV) to the subject;
    wherein the subject demonstrates an enhanced immune response to PRRSV as compared to a subject administered only the vaccine, and
    wherein the subject is administered the *E. faecium* at least 5 days prior to vaccination, at the time of vaccination, and/or continuing for at least 2 weeks after vaccination.

2. The method of claim 1, wherein the subject is an animal species selected from the group consisting of a domesticated animal, a farm animal, a human, and an aquatic animal.

3. The method of claim 1, wherein the therapeutically effective amount of the at least one dopamine producing probiotic is from about $10^4$ CFU/g of probiotic to about $10^{14}$ CFU/g of probiotic.

4. The method of claim 1, wherein the dopamine producing probiotic further comprises *Vagococcus* spp.

5. The method of claim 1, wherein said dopamine producing probiotic further comprises a genetically modified bacterium engineered to produce dopamine and/or L-dopa, wherein the genetically modified bacterium is administered into animal feed by encapsulation.

6. The method of claim 1, wherein the therapeutically effective amount of L-dopa is administered into animal feed.

7. The method of claim 1, wherein the therapeutically effective amount of L-dopa is from about 0.1 mg/kg animal feed to about 10 g/kg animal feed.

8. The method of claim 1, wherein the at least one dopamine producing probiotic and L-dopa are co-administered in a single delivery system.

9. The method of claim 8, wherein the single delivery system comprises a co-formulation and/or co-packaged formulation.

\* \* \* \* \*